(12) United States Patent
Hallahan et al.

(10) Patent No.: US 7,402,392 B2
(45) Date of Patent: *Jul. 22, 2008

(54) IN VIVO PANNING FOR LIGANDS TO RADIATION-INDUCED MOLECULES

(75) Inventors: Dennis E. Hallahan, Nashville, TN (US); Shimian Qu, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/259,087

(22) Filed: Sep. 27, 2002

(65) Prior Publication Data

US 2003/0130190 A1 Jul. 10, 2003

Related U.S. Application Data

(60) Provisional application No. 60/328,123, filed on Oct. 3, 2001.

(51) Int. Cl.
*G01N 33/53* (2006.01)
*G01N 33/569* (2006.01)

(52) U.S. Cl. .............. 435/7.1; 435/6; 435/5; 435/4; 435/DIG. 4; 435/DIG. 2; 435/235.1

(58) Field of Classification Search ............ 435/7.1, 435/6, 5, 4, DIG. 2, DIG. 4
See application file for complete search history.

(56) References Cited

U.S. PATENT DOCUMENTS

| | | | |
|---|---|---|---|
| 6,159,443 A | 12/2000 | Hallahan | |
| 7,018,615 B2 * | 3/2006 | Ruoslahti et al. | 424/9.1 |
| 7,056,506 B2 * | 6/2006 | Varner | 424/130.1 |
| 7,138,238 B2 * | 11/2006 | Vodyanoy et al. | 435/7.1 |
| 2002/0164663 A1 * | 11/2002 | Fuqua et al. | 435/7.23 |
| 2003/0083261 A1 * | 5/2003 | Yu et al. | 514/13 |

OTHER PUBLICATIONS

Pasqualini et al, Molecular Psychiatry, 1996,1, 423.*
Barry et al, Nature Medicine, 2(3) (Mar. 1996), 299-305.*
International Search Report for corresponding PCT Appl. No. PCT/US02/30917 dated Feb. 10, 2005.
Hallahan et al., "Targeting Drug Delivery to Radiation-induced Neoantigens in Tumor Microvasculature", *Journal of Controlled Release*, 74: 183-191, 2001.
Hallahan et al., "X-Ray-induced P-Seectin Localization to the Lumen of Tumor Blood Vessels", *Cancer Research*, 58: 5216-5220, Nov. 15, 1998.
Lieberman et al., "A Human Homolog of the Schizosaccharomyces Pombe rad9 Check Point Control Gene", *Proceedings of the National Academy of Sciences*, 93: 13890-13895, Nov. 1996.
Database HCAPLUS on STN, ACS (Columbus, OH, USA) No. 2001:661624, Xu et al., "Cell Cycle Proteins PP5 Associated with rad9 and Uses in Screening for a Bioactive Agent", Abstract, WO 01/64913, see Registry No. 263887-03-2, human gene rad9, for SEQ ID No. 8.
Database HCAPLUS on STN, ACS (Columbus, OH, USA) No. 1997:513697, Dolganov, "The Human rad50 and Septin-2 Genes and their Roles in Myelodysplastic diseases and their Diagnostic and Therapeutic Uses", Abstract, WO 97/27284, see Registry No. 194813-18-8, human clone B15.2, for SEQBID No. 8.
Database HCAPLUS on STN, ACS (Columbus, OH, USA) No. 2000:573954, Kastan et al., "ATM Kinase Modulation for Screening and Therapies", WO 00/47760, see Registry No. 288259-02-9 for SEQ ID No. 8 and 10 and Registry No. 288259-18-7 for SEQ ID No. 13.
Database HCAPLUS on STN, ACS (Columbus, OH, USA) No. 1998:248017, Kurnik et al., "Prospective Study of Atrial Natriuretic Peptide for the Prevention of Radio-Contrast-Induced Nephropathy", Abstract, *American Journal of Kidney Diseases*, 1998, see Registry No. 95896-08-5, atrial natriuretic peptide-25, for SEQ ID No. 11.
Database HCAPLUS on STN, ACS (Columbus, OH, USA) No. 1998:365000, Croce et al., "Cloning of Human rad54 Gene Homolog and its Diagnostic and Therapeutic uses", EP 844,305, see Registry No. 208601-90-5, human rad54, for SEQ ID No. 12.

* cited by examiner

*Primary Examiner*—T. D. Wessendorf
(74) *Attorney, Agent, or Firm*—Jenkins, Wilson, Taylor & Hunt, P.A.

(57) ABSTRACT

A method for identifying a molecule that binds an irradiated tumor in a subject and molecules identified thereby. The method includes the steps of: (a) exposing a tumor to ionizing radiation; (b) administering to a subject a library of diverse molecules; and (c) isolating from the tumor one or more molecules of the library of diverse molecules, whereby a molecule that binds an irradiated tumor is identified. Also provided are therapeutic and diagnostic methods using targeting ligands that bind an irradiated tumor.

22 Claims, No Drawings

SEQUENCE LISTING

<160> NUMBER OF SEQ ID NOS: 20

<210> SEQ ID NO 1
<211> LENGTH: 8
<212> TYPE: PRT
<213> ORGANISM: Artificial Sequence
<220> FEATURE:
<223> OTHER INFORMATION: Artificial peptide ligand number 1

<400> SEQUENCE: 1

Asn His Val Gly Gly Ser Ser Val

```
<210> SEQ ID NO 2
<211> LENGTH: 10
<212> TYPE: PRT
<213> ORGANISM: Artificial Sequence
<220> FEATURE:
<223> OTHER INFORMATION: Artificial peptide ligand number 2

<400> SEQUENCE: 2

Asn Ser Leu Arg Gly Asp Gly Ser Ser Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Artificial peptide ligand number 3

<400> SEQUENCE: 3

Asn Ser Val Arg Gly Ser Gly Ser Gly Val
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Artificial peptide ligand number 4

<400> SEQUENCE: 4

Asn Ser Val Gly Ser Arg Val
1               5

<210> SEQ ID NO 5
<211> LENGTH: 9
<212> TYPE: PRT
<213> ORGANISM: Artificial Sequence
<220> FEATURE:
<223> OTHER INFORMATION: Artificial peptide ligand number 5

<400> SEQUENCE: 5

Ser Leu Arg Gly Asp Gly Ser Ser Val
1               5

<210> SEQ ID NO 6
<211> LENGTH: 7
<212> TYPE: PRT
<213> ORGANISM: Artificial Sequence
<220> FEATURE:
<223> OTHER INFORMATION: Artificial peptide ligand number 6

<400> SEQUENCE: 6

Arg Gly Asp Gly Ser Ser Val
1               5

<210> SEQ ID NO 7
<211> LENGTH: 4
<212> TYPE: PRT
<213> ORGANISM: Artificial Sequence
<220> FEATURE:
<223> OTHER INFORMATION: Artificial peptide ligand number 7

<400> SEQUENCE: 7

Gly Ser Arg Val
1
```

<210> SEQ ID NO 8
<211> LENGTH: 4
<212> TYPE: PRT
<213> ORGANISM: Artificial Sequence
<220> FEATURE:
<223> OTHER INFORMATION: Artificial peptide ligand number 8
<220> FEATURE:
<221> NAME/KEY: MISC_FEATURE
<222> LOCATION: (1)..(4)
<223> OTHER INFORMATION: Xaa is any amino acid

<400> SEQUENCE: 8

Gly Ser Xaa Val
1

<210> SEQ ID NO 9
<211> LENGTH: 8
<212> TYPE: PRT
<213> ORGANISM: Artificial Sequence
<220> FEATURE:
<223> OTHER INFORMATION: Artificial peptide ligand number 9
<220> FEATURE:
<221> NAME/KEY: MISC_FEATURE
<222> LOCATION: (1)..(8)
<223> OTHER INFORMATION: Xaa is any amino acid

<400> SEQUENCE: 9

Asn Ser Xaa Arg Gly Xaa Gly Ser
1               5

<210> SEQ ID NO 10
<211> LENGTH: 3
<212> TYPE: PRT
<213> ORGANISM: Artificial Sequence
<220> FEATURE:
<223> OTHER INFORMATION: Artificial peptide ligand number 10

<400> SEQUENCE: 10

Asn Ser Val
1

<210> SEQ ID NO 11
<211> LENGTH: 4
<212> TYPE: PRT
<213> ORGANISM: Artificial Sequence
<220> FEATURE:
<223> OTHER INFORMATION: Artificial peptide ligand number 11
<220> FEATURE:
<221> NAME/KEY: MISC_FEATURE
<222> LOCATION: (1)..(4)
<223> OTHER INFORMATION: Xaa is any amino acid

<400> SEQUENCE: 11

Asn Ser Xaa Arg
1

<210> SEQ ID NO 12
<211> LENGTH: 4
<212> TYPE: PRT
<213> ORGANISM: Artificial Sequence
<220> FEATURE:
<223> OTHER INFORMATION: Artificial peptide ligand number 12
<220> FEATURE:
<221> NAME/KEY: MISC_FEATURE
<222> LOCATION: (1)..(4)
<223> OTHER INFORMATION: Xaa is any amino acid

<400> SEQUENCE: 12

```
Asn Xaa Val Gly
 1

<210> SEQ ID NO 13
<211> LENGTH: 4
<212> TYPE: PRT
<213> ORGANISM: Artificial Sequence
<220> FEATURE:
<223> OTHER INFORMATION: Artificial peptide ligand number 13

<400> SEQUENCE: 13

Gly Ser Ser Val
 1

<210> SEQ ID NO 14
<211> LENGTH: 20
<212> TYPE: DNA
<213> ORGANISM: T7 bacteriophage

<400> SEQUENCE: 14
agcggaccag attatcgcta                                                     20

<210> SEQ ID NO 15
<211> LENGTH: 19
<212> TYPE: DNA
<213> ORGANISM: T7 bacteriophage

<400> SEQUENCE: 15
aaccctcaag acccgttta                                                      19

<210> SEQ ID NO 16
<211> LENGTH: 12
<212> TYPE: PRT
<213> ORGANISM: Artificial Sequence
<220> FEATURE:
<223> OTHER INFORMATION: Artificial peptide ligand number 16

<400> SEQUENCE: 16

His His Cys Gly Gly Ala Lys Gln Ala Gly Asp Val
 1               5                  10

<210> SEQ ID NO 17
<211> LENGTH: 726
<212> TYPE: DNA
<213> ORGANISM: Artificial Sequence
<220> FEATURE:
<223> OTHER INFORMATION: Artificial antibody ligand number 1
<220> FEATURE:
<221> NAME/KEY: CDS
<222> LOCATION: (1)..(726)
<223> OTHER INFORMATION:

<400> SEQUENCE: 17 atg gcc cag gtg aaa ctg cag cag tct ggg gct gag ctt gtg atg cct        48
Met Ala Gln Val Lys Leu Gln Gln Ser Gly Ala Glu Leu Val Met Pro
 1               5                  10                  15 ggg gct tca gtg aag atg tcc tgc aag gct tct ggc tac aca ttc act        96
Gly Ala Ser Val Lys Met Ser Cys Lys Ala Ser Gly Tyr Thr Phe Thr
                20                  25                  30 gac tac tgg atg cac tgg gtg aag cag agg cct gga caa ggc ctt gag       144
Asp Tyr Trp Met His Trp Val Lys Gln Arg Pro Gly Gln Gly Leu Glu
            35                  40                  45 tgg atc gga gcg att gat act tct gat agt tat act agc tac aat caa       192
Trp Ile Gly Ala Ile Asp Thr Ser Asp Ser Tyr Thr Ser Tyr Asn Gln
        50                  55                  60
```

```
aag ttc aag ggc aag gcc aca ttg act gta gac gaa tcc tcc agc aca      240
Lys Phe Lys Gly Lys Ala Thr Leu Thr Val Asp Glu Ser Ser Ser Thr
 65                  70                  75                  80 gcc tac atg cag ctc agc agc ctg aca tct gag gac tct gcg gtc tat      288
Ala Tyr Met Gln Leu Ser Ser Leu Thr Ser Glu Asp Ser Ala Val Tyr
                 85                  90                  95 tac tgt gca aga aga ggc tac tat agc gca ttt gat tac tgg ggc caa      336
Tyr Cys Ala Arg Arg Gly Tyr Tyr Ser Ala Phe Asp Tyr Trp Gly Gln
            100                 105                 110 ggg act acg gtc acc gtc tcc tca ggt gga ggc ggt tca ggc gga ggt      384
Gly Thr Thr Val Thr Val Ser Ser Gly Gly Gly Gly Ser Gly Gly Gly
        115                 120                 125 ggc tct ggc ggt ggc gga tcg gac att gag ctc acc cag tct cca aca      432
Gly Ser Gly Gly Gly Gly Ser Asp Ile Glu Leu Thr Gln Ser Pro Thr
    130                 135                 140 acc atg gct gca tct cca gga gag aag gtc acc atc acc tgc cgt gcc      480
Thr Met Ala Ala Ser Pro Gly Glu Lys Val Thr Ile Thr Cys Arg Ala
145                 150                 155                 160 agc tca agt gta agc tac atg cac tgg ttc cag cag aag tca ggc acc      528
Ser Ser Ser Val Ser Tyr Met His Trp Phe Gln Gln Lys Ser Gly Thr
                165                 170                 175 tcc ccc aaa ccc tgg att tat gac aca tcc aag ctg gct tct gga gtc      576
Ser Pro Lys Pro Trp Ile Tyr Asp Thr Ser Lys Leu Ala Ser Gly Val
            180                 185                 190 cca gat cgc ttc agt ggc agt ggg tct ggg acc tct tat tct ctc aca      624
Pro Asp Arg Phe Ser Gly Ser Gly Ser Gly Thr Ser Tyr Ser Leu Thr
        195                 200                 205 atc agc tcc atg gag gct gaa gat gct gct act tat tac tgt ctg cag      672
Ile Ser Ser Met Glu Ala Glu Asp Ala Ala Thr Tyr Tyr Cys Leu Gln
    210                 215                 220 agg agt agt tac ccg tac acg ttt gga gct ggc acc aag ctg gaa atc      720
Arg Ser Ser Tyr Pro Tyr Thr Phe Gly Ala Gly Thr Lys Leu Glu Ile
225                 230                 235                 240 aaa cgg                                                              726
Lys Arg <210> SEQ ID NO 18
<211> LENGTH: 242
<212> TYPE: PRT
<213> ORGANISM: Artificial Sequence
<220> FEATURE:
<223> OTHER INFORMATION: Artificial antibody ligand number 1

<400> SEQUENCE: 18

Met Ala Gln Val Lys Leu Gln Gln Ser Gly Ala Glu Leu Val Met Pro
1               5                   10                  15

Gly Ala Ser Val Lys Met Ser Cys Lys Ala Ser Gly Tyr Thr Phe Thr
            20                  25                  30

Asp Tyr Trp Met His Trp Val Lys Gln Arg Pro Gly Gln Gly Leu Glu
        35                  40                  45

Trp Ile Gly Ala Ile Asp Thr Ser Asp Ser Tyr Thr Ser Tyr Asn Gln
    50                  55                  60

Lys Phe Lys Gly Lys Ala Thr Leu Thr Val Asp Glu Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Arg Gly Tyr Tyr Ser Ala Phe Asp Tyr Trp Gly Gln
            100                 105                 110
```

```
Gly Thr Thr Val Thr Val Ser Ser Gly Gly Gly Ser Gly Gly Gly
        115                 120                 125

Gly Ser Gly Gly Gly Ser Asp Ile Glu Leu Thr Gln Ser Pro Thr
        130                 135                 140

Thr Met Ala Ala Ser Pro Gly Glu Lys Val Thr Ile Thr Cys Arg Ala
145                 150                 155                 160

Ser Ser Ser Val Ser Tyr Met His Trp Phe Gln Gln Lys Ser Gly Thr
                165                 170                 175

Ser Pro Lys Pro Trp Ile Tyr Asp Thr Ser Lys Leu Ala Ser Gly Val
            180                 185                 190

Pro Asp Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys Leu Gln
        210                 215                 220

Arg Ser Ser Tyr Pro Tyr Thr Phe Gly Ala Gly Thr Lys Leu Glu Ile
225                 230                 235                 240

Lys Arg

<210> SEQ ID NO 19
<211> LENGTH: 726
<212> TYPE: DNA
<213> ORGANISM: Artificial Sequence
<220> FEATURE:
<223> OTHER INFORMATION: Artificial antibody ligand number 2
<220> FEATURE:
<221> NAME/KEY: CDS
<222> LOCATION: (1)..(726)
<223> OTHER INFORMATION:

<400> SEQUENCE: 19 atg gcc cag gtc aag ctg cag cag tca gga cct gag ctg gta aag cct        48
Met Ala Gln Val Lys Leu Gln Gln Ser Gly Pro Glu Leu Val Lys Pro
1               5                   10                  15 ggg gct tca gtg aag atg tcc tgc aag gct tct gga tac aca ttc act        96
Gly Ala Ser Val Lys Met Ser Cys Lys Ala Ser Gly Tyr Thr Phe Thr
            20                  25                  30 agc tat gtt atg cac tgg gtg aag cag aag cct ggg cag ggc ctt gag       144
Ser Tyr Val Met His Trp Val Lys Gln Lys Pro Gly Gln Gly Leu Glu
        35                  40                  45 tgg att gga tat att aat cct tac aat gat ggt act aag tac aat gag       192
Trp Ile Gly Tyr Ile Asn Pro Tyr Asn Asp Gly Thr Lys Tyr Asn Glu
    50                  55                  60 aag ttc aaa ggc aag gcc gca ctg act tca gac aaa tcc tcc agc aca       240
Lys Phe Lys Gly Lys Ala Ala Leu Thr Ser Asp Lys Ser Ser Ser Thr
65                  70                  75                  80 gcc tac atg gag ctc agc agc ctg acc tct gag gac tct gcg gtc tat       288
Ala Tyr Met Glu Leu Ser Ser Leu Thr Ser Glu Asp Ser Ala Val Tyr
                85                  90                  95 tac tgt gca aga ttt ggt aac tac ggt gct ttg gac tac tgg ggc caa       336
Tyr Cys Ala Arg Phe Gly Asn Tyr Gly Ala Leu Asp Tyr Trp Gly Gln
            100                 105                 110 ggg acc acg gtc acc gtc tcc tca ggt gga ggc ggt tca ggc gga ggt       384
Gly Thr Thr Val Thr Val Ser Ser Gly Gly Gly Gly Ser Gly Gly Gly
        115                 120                 125 ggc tct ggc ggt ggc gga tcg gac att gag ctc acc cag tct cca aca       432
Gly Ser Gly Gly Gly Gly Ser Asp Ile Glu Leu Thr Gln Ser Pro Thr
    130                 135                 140
```

-continued

```
atc atg tct gca tct cca ggg gag aag gtc acc ata acc tgc agt gcc    480
Ile Met Ser Ala Ser Pro Gly Glu Lys Val Thr Ile Thr Cys Ser Ala
145                 150                 155                 160 agc tca agt gta agt tac atg cac tgg ttc cag cag aag cca ggc act    528
Ser Ser Ser Val Ser Tyr Met His Trp Phe Gln Gln Lys Pro Gly Thr
                165                 170                 175 tct ccc aaa ccc tgg att tat ggc aca tcc aac ctg gct tct gga gtc    576
Ser Pro Lys Pro Trp Ile Tyr Gly Thr Ser Asn Leu Ala Ser Gly Val
            180                 185                 190 cct gtt cgc ttc agt ggc agt gga tct ggg acc tct tat tct ctc aca    624
Pro Val Arg Phe Ser Gly Ser Gly Ser Gly Thr Ser Tyr Ser Leu Thr
        195                 200                 205 atc agc agc atg gag gct gaa gat gct gcc act tat tac tgt caa cag    672
Ile Ser Ser Met Glu Ala Glu Asp Ala Ala Thr Tyr Tyr Cys Gln Gln
    210                 215                 220 tgg agt agt tac cca ctc acg ttc gga ggg ggg acc aag ctg gaa ata    720
Trp Ser Ser Tyr Pro Leu Thr Phe Gly Gly Gly Thr Lys Leu Glu Ile
225                 230                 235                 240 aaa cgg                                                            726
Lys Arg

<210> SEQ ID NO 20
<211> LENGTH: 242
<212> TYPE: PRT
<213> ORGANISM: Artificial Sequence
<220> FEATURE:
<223> OTHER INFORMATION: Artificial antibody ligand number 2

<400> SEQUENCE: 20

Met Ala Gln Val Lys Leu Gln Gln Ser Gly Pro Glu Leu Val Lys Pro
1               5                   10                  15

Gly Ala Ser Val Lys Met Ser Cys Lys Ala Ser Gly Tyr Thr Phe Thr
                20                  25                  30

Ser Tyr Val Met His Trp Val Lys Gln Lys Pro Gly Gln Gly Leu Glu
            35                  40                  45

Trp Ile Gly Tyr Ile Asn Pro Tyr Asn Asp Gly Thr Lys Tyr Asn Glu
        50                  55                  60

Lys Phe Lys Gly Lys Ala Ala Leu Thr Ser Asp Lys Ser Ser Ser Thr
65                  70                  75                  80

Ala Tyr Met Glu Leu Ser Ser Leu Thr Ser Glu Asp Ser Ala Val Tyr
                85                  90                  95

Tyr Cys Ala Arg Phe Gly Asn Tyr Gly Ala Leu Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Glu Leu Thr Gln Ser Pro Thr
    130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Pro Trp Ile Tyr Gly Thr Ser Asn Leu Ala Ser Gly Val
            180                 185                 190

Pro Val Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys Gln Gln
    210                 215                 220
```

```
-continued

Trp Ser Ser Tyr Pro Leu Thr Phe Gly Gly Gly Thr Lys Leu Glu Ile
225                 230                 235                 240

Lys Arg
```

IN VIVO PANNING FOR LIGANDS TO RADIATION-INDUCED MOLECULES

CROSS REFERENCE TO RELATED APPLICATIONS

This application is based on and claims priority to U.S. Provisional Patent application Ser. No. 60/328,123, filed Oct. 3, 2001, herein incorporated by reference in its entirety.

GRANT STATEMENT

This work was supported by grants CA58508, CA70937, CA89888, CA89674, and CA90949 from the U.S. National Institute of Health. Thus, the U.S. government has certain rights in the invention.

FIELD OF THE INVENTION

The present invention generally relates to ligands for x-ray guided drug delivery. More particularly, the invention provides a method for in vivo panning of diverse molecules for isolation of targeting ligands that specifically bind an irradiated tumor. Also provided are novel targeting ligands identified by the panning method, and therapeutic and diagnostic uses of the same.

TABLE OF ABBREVIATIONS

AR—autoradiography
CPM—counts per minute
CT—computerized tomography
HPLC—high performance liquid chromatography
IP—imaging plate
LUER—low energy high resolution
MRI—magnetic resonance imaging
NM—nuclear magnetic
OD—optical density
PCR—Polymerase Chain Reaction
PET—positron emission spectroscopy
PFU—plaque forming unit
ROI—region of interest
SPECT—single photon emission computed tomography

BACKGROUND OF THE INVENTION

Tumor-specific drug delivery has the potential to minimize toxicity to normal tissues and improve the bioavailability of therapeutic agents to tumor cells (Hallahan et al., 1995b; Arap et al., 1998). Targeting ligands include antibodies and peptides that accumulate in tumors by specific binding to target molecules present on tumor vasculature, endothelial cells associated with tumor vasculature, and tumor cells. Effective target molecules are generally cell surface receptors or other molecules present at the exterior of tumor cells such that they are accessible to targeting ligands (Hallahan et al., 2001a).

Existing site-specific drug delivery systems include ligands that recognize a tumor marker such as Her2/neu (v-erb-b2 avian erythroblastic leukemia viral oncogene homologue 2), CEA (carcinoembryonic antigen) (Ito et al., 1991), and breast cancer antigens (Manome et al., 1994; Kirpotin et al., 1997; Becerril et al., 1999). See also PCT International Publication No. WO 98/10795. In an effort to identify ligands that are capable of targeting to multiple tumor types, targeting ligands have been developed that bind to target molecules present on tumor vasculature (Baillie et al., 1995; Pasqualini & Ruoslahti, 1996; Arap et al., 1998; Burg et al., 1999; Ellerby et al., 1999).

Despite these advances, current methods for targeted drug delivery are hindered by targeting ligands that also bind normal tissues and/or a lack of targeting ligands that bind multiple tumor types. Ideally, a targeting molecule should display specific targeting in the absence of substantial binding to normal tissues, and a capacity for targeting to a variety of tumor types and stages. Thus, there exists a long-felt need in the art for methods to achieve site-specific, tumoral delivery of therapeutic and/or diagnostic agents.

To meet this need, the present invention provides a method for identifying ligands that bind to irradiated tumors. Such ligands are useful for x-ray guided drug delivery, among other applications.

SUMMARY OF INVENTION

The present invention provides methods for identifying a molecule that binds to an irradiated tumor in a subject. In one embodiment of the invention, the method comprises: (a) exposing a tumor to ionizing radiation; (b) administering to a subject a library of diverse molecules; and (c) isolating one or more molecules of the library from the tumor, whereby a molecule that binds an irradiated tumor is identified.

In another embodiment of the invention, the method for identifying a molecule that binds an irradiated tumor comprises: (a) exposing a tumor and a control tissue to ionizing radiation; (b) administering to the tumor and to the control tissue a library of diverse molecules; (c) detecting one or more molecules of the library that bind to the tumor and that substantially lack binding to the control tissue, whereby a molecule that binds an irradiated tumor is identified. The method can further comprise: (a) isolating the tumor and the control tissue, and (b) administering the library to the tumor and to the control tissue in vitro.

The in vivo panning methods of the present invention can further comprise administering the library to isolated tumor cells or to isolated proteins prior to administering the library to a subject or to a tumor. For example, in vitro panning methods can be performed to select ligands that bind to particular tumor neoantigens, followed by performance of the in vivo panning methods as disclosed herein.

When performing the in vivo panning methods of the invention, each of the steps of exposing, administering, and isolating can be repeated one or more times to modify and preferably improve ligand selection.

A library useful for in vivo panning as disclosed herein can comprise in one example a library of ten or more diverse molecules, in another example a library of one hundred or more diverse molecules, and in yet another example a library of one billion or more diverse molecules. Representative diverse molecules include peptides, peptide mimetics, proteins, antibodies or fragments thereof, small molecules, nucleic acids, and combinations thereof. In one embodiment of the invention, a library of peptides, antibodies, or a combination thereof is used for in vivo panning. A library can further comprise a library of diverse molecules that is recovered following in vitro panning.

Also provided are targeting ligands identified by performing the method. Representative peptide ligands are set forth as SEQ ID NOs:1-13. Also provided are cyclized and derivatized variants of peptide ligands set forth as SEQ ID NOs:1-13. Representative antibody ligands comprise single chain antibody polypeptides comprising: (a) a polypeptide comprising an amino acid sequence of SEQ ID NO:18 or 20; (b) a polypeptide comprising an amino acid sequence substantially similar to SEQ ID NO:18 or 20; (c) a polypeptide encoded by a nucleotide sequence of SEQ ID NO:17 or 19; (d) a polypeptide encoded by a nucleotide sequence substantially similar to SEQ ID NO:17 or 19; or (e) combinations thereof. The provided peptide ligands can be used in the methods and compositions of the present invention, as disclosed herein below.

The peptide ligands of the present invention are useful for x-ray-guided delivery to a tumor in a subject. A tumor can comprise a primary or a metastasized tumor, including but not limited to a tumor selected from the group consisting of bladder carcinoma, breast carcinoma, cervical carcinoma, cholangiocarcinoma, colorectal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, a head tumor, a neck tumor, and a solid tumor. In one example, a targeting ligand binds to an irradiated glioma, melanoma, or a Lewis Lung carcinoma.

An exemplary peptide ligand of the invention can bind to an irradiated tumor of two or more tumor types, or in another example three or more tumor types. In yet another example, a targeting ligand can bind to an irradiated glioma, melanoma, and a Lewis Lung carcinoma.

The present invention also provides a method for preparing a composition for x-ray-guided drug delivery. The method comprises: (a) performing in vivo panning, whereby a ligand that binds a radiation-inducible tumor molecule is identified; and (b) conjugating the ligand to a drug, whereby a composition for x-ray-guided drug delivery is prepared.

The present invention thus provides a therapeutic composition, a diagnostic composition, or a combination thereof, comprising the disclosed peptide ligands. Such compositions can optionally include a drug carrier, for example a viral vector, a liposome, a plasmid, a microcapsule, and combinations thereof. Drug carriers include but are not limited to liposomes and microspheres.

A diagnostic composition of the invention comprises a targeting peptide and a detectable label. A detectable label can comprise a label that can be detected in vivo, for example by using any one of techniques including but not limited to magnetic resonance imaging, scintigraphic imaging, ultrasound, or fluorescence. When a radionuclide label is employed, for example $^{131}$I or $^{99m}$Tc, the label can be detected using PET, SPECT, gamma camera imaging, or rectilinear scanning. Alternatively, a diagnostic composition of the invention can comprise a label such as a fluorophore, an epitope, or a radioactive label.

A therapeutic composition of the invention comprises a therapeutic agent and a targeting peptide. Representative therapeutic agents include a radionuclide, a cytotoxin, a therapeutic gene, and a chemotherapeutic agent. A therapeutic composition of the invention can further comprise a detectable label, in one example a label that can be detected in vivo, to monitor the biodistribution of the composition following administration to a subject.

The present invention also provides methods for diagnosing a tumor in a subject. The method relies on the capacity of the disclosed peptide ligands to bind to an irradiated tumor. The binding reaction can be performed in vivo or in vitro.

Thus, in one embodiment of the invention, a method for tumor diagnosis comprises: (a) exposing a suspected tumor to ionizing radiation; (b) administering to the subject one or more targeting ligands identified by in vivo panning, wherein the one or more targeting ligands binds an irradiated tumor, and wherein the peptide comprises a detectable label; and (c) detecting the detectable label, whereby a tumor is diagnosed.

In another embodiment, a method for diagnosing a tumor in a subject comprises: (a) exposing a suspected tumor to ionizing radiation; (b) isolating the suspected tumor, or fraction thereof; (c) contacting the suspected tumor with one or more targeting ligands, wherein the one or more targeting ligands binds an irradiated tumor, and wherein the peptide comprises a detectable label; and (d) detecting the detectable label, whereby the tumor is diagnosed. In one example, the peptide can bind to an irradiated tumor.

For detection of a tumor in vitro (using an isolated tumor), the isolating can comprise biopsing a suspected tumor. The isolating can be performed prior to or subsequent to exposing the suspected tumor to ionizing radiation.

The diagnostic methods of the present invention can further comprise simultaneously detecting two or more tumors in a subject, including two or more tumors comprising two or more tumor types.

The present invention further provides a method for x-ray-guided delivery of a therapeutic composition, a diagnostic composition, and a combination thereof, to a tumor in a subject. The method comprises: (a) exposing the tumor to ionizing radiation; and (b) administering to the subject a therapeutic composition, a diagnostic composition, or a combination thereof, wherein the composition comprises a targeting ligand identified by in vivo panning; whereby the therapeutic composition, the diagnostic composition, or the combination thereof, is selectively targeted to the tumor.

In accordance with the methods for in vivo panning, tumor diagnosis, and x-ray-guided drug delivery disclosed herein, in one example an amount of radiation exposure can comprise less than about 2 Gy ionizing radiation. The invention further encompasses exposing a tumor or suspected tumor in one example to at least about 2 Gy ionizing radiation, and in another example to about 10-20 Gy ionizing radiation. In one example, a tumor is irradiated 0 hours to about 24 hours, and in another example about 4 hours to about 24 hours, prior to administration to a subject of a library or a therapeutic composition, a diagnostic composition, or combination thereof.

The disclosed methods for tumor diagnosis and x-ray-guided drug delivery are suitable for detection and delivery of a therapeutic composition, a diagnostic composition, or a combination thereof in a warm-blooded vertebrate subject, preferably a human subject.

The present invention also provides a method for identifying a radiation-induced target molecule. The method comprises: (a) providing a targeting ligand identified by in vivo panning, wherein the peptide binds to an irradiated tumor; (b) exposing the targeting ligand to one or more candidate target molecules; and (c) determining selective binding of the one or more candidate target molecules to the targeting ligand, whereby a radiation-induced target molecule is identified. The molecule bound by the peptide can comprise a molecule present on a tumor cell, an endothelial cell associated with tumor vasculature, or a blood component. Also provided are target molecules identified by the method.

Accordingly, it is an object of the present invention to provide novel targeting ligands that bind irradiated tumors, methods for identifying the same, and therapeutic and/or diagnostic methods using the same. This and others objects are achieved in whole or in part by the present invention.

An object of the invention having been stated above, other objects and advantages of the present invention will become apparent to those skilled in the art after a study of the following description of the invention and non-limiting Examples.

DETAILED DESCRIPTION OF THE INVENTION

I. Definitions

While the following terms are believed to be well understood by one of ordinary skill in the art, the following definitions are set forth to facilitate explanation of the invention.

The term "ligand" as used herein refers to a molecule or other chemical entity having a capacity for binding to a target. A ligand can comprise a peptide, an oligomer, a nucleic acid (e.g., an aptamer), a small molecule (e.g., a chemical compound), an antibody or fragment thereof, a nucleic acid-protein fusion, and/or any other affinity agent.

The term "small molecule" as used herein refers to a compound, for example an organic compound, with a molecular weight in one example of less than about 1,000 daltons, in another example less than about 750 daltons, in another example less than about 600 daltons, and in yet another example less than about 500 daltons. A small molecule also has in one example a computed log octanol-water partition coefficient in the range of about −4 to about +14, more preferably in the range of about −2 to about +7.5.

The term "target tissue" as used herein refers to an intended site for accumulation of a ligand following administration to a subject. For example, the methods of the present invention employ a target tissue comprising an irradiated tumor.

The term "control tissue" as used herein refers to a site suspected to substantially lack binding and/or accumulation of an administered ligand. For example, in accordance with the methods of the present invention, a non-irradiated tumor and a non-cancerous tissue are control tissues.

The terms "target" or "target molecule" as used herein each refer to any substance that is specifically bound by a ligand. Thus, the term "target molecule" encompasses macromolecules including but not limited to proteins, nucleic acids, carbohydrates, lipids, and complexes thereof.

The terms "radiation-induced target" and "radiation-induced tumor target" as used herein each refer to a target molecule in a tumor whose expression, localization, or ligand-binding capacity is induced by radiation. Such a target molecule can comprise a molecule at the surface of a tumor cell, within a tumor cell, or in the extracellular matrix surrounding a tumor cell. Alternatively, a target molecule can comprise a molecule present at the surface of or within a vascular endothelial cell, or at the surface of or within a blood component such as a platelet or a leukocyte.

The term "induce", as used herein to refer to changes resulting from radiation exposure, encompasses activation of gene transcription or regulated release of proteins from cellular storage reservoirs to vascular endothelium. Alternatively, induction can refer to a process of conformational change, also called activation, such as that displayed by the glycoprotein IIb/IIIa integrin receptor upon radiation exposure (Staba et al., 2000; Hallahan et al., 2001a). See also U.S. Pat. No. 6,159,443.

The terms "targeting" or "homing", as used herein to describe the in vivo activity of a ligand following administration to a subject, each refer to the preferential movement and/or accumulation of a ligand in a target tissue as compared with a control tissue.

The terms "selective targeting" of "selective homing" as used herein each refer to a preferential localization of a ligand that results in an amount of ligand in a target tissue that is in one example about 2-fold greater than an amount of ligand in a control tissue, in another example an amount that is about 5-fold or greater, and in yet another example an amount that is about 10-fold or greater. The terms "selective targeting" and "selective homing" also refer to binding or accumulation of a ligand in a target tissue concomitant with an absence of targeting to a control tissue, preferably the absence of targeting to all control tissues.

The term "absence of targeting" is used herein to describe substantially no binding or accumulation of a ligand in all control tissues where an amount of ligand is detectable.

The terms "targeting ligand", "targeting molecule", "homing ligand", and "homing molecule" as used herein each refer to a ligand that displays targeting activity. In one example, a targeting ligand displays selective targeting.

The term "binding" refers to an affinity between two molecules, for example, a ligand and a target molecule. As used herein, "binding" means a preferential binding of one molecule for another in a mixture of molecules. The binding of a ligand to a target molecule can be considered specific if the binding affinity is about $1\times10^4$ $M^{-1}$ to about $1\times10^6$ $M^{-1}$ or greater.

The phrase "specifically (or selectively) binds", when referring to the binding capacity of a ligand, refers to a binding reaction which is determinative of the presence of the protein in a heterogeneous population of proteins and other biological materials. The phrase "specifically binds" also refers to selectively targeting, as defined herein above.

The phases "substantially lack binding" or "substantially no binding", as used herein to describe binding of a ligand in a control tissue, refers to a level of binding that encompasses non-specific or background binding, but does not include specific binding.

The term "tumor" as used herein refers to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas.

The term "subject" as used herein refers to any invertebrate or vertebrate species. The methods of the present invention are particularly useful in the treatment and diagnosis of warm-blooded vertebrates. Thus, the invention concerns mammals and birds. More particularly contemplated is the treatment and/or diagnosis of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

The term "about", as used herein when referring to a measurable value such as an amount of weight, time, dose (e.g. radiation dose), etc. is meant to encompass variations of in one example ±20% or ±0%, in another example ±5%, in another example ±1%, and in yet another example ±0.1% from the specified amount, as such variations are appropriate to perform the disclosed method.

II. X-ray Guided Drug Delivery Using Peptide Ligands

Ionizing radiation induces proteins in tumor vascular endothelium through transcriptional induction and/or post-translational modification of cell adhesion molecules such as integrins (Hallahan et al., 1995a; Hallahan et al., 1996; Hallahan et al., 1998; Hallahan & Virudachalam, 1999). For example, radiation induces activation of the integrin $\alpha_{2b}\beta_3$, also called the fibrinogen receptor, on platelets. The induced molecules can serve as binding sites for targeting ligands.

Although several radiation-induced molecules within tumor blood vessels have been identified and characterized, the $\alpha_{2b}\beta_3$ target for drug delivery achieves the greatest site-specific peptide binding within irradiated tumor blood vessels. $^{131}$I-labeled fibrinogen binds specifically to tumors following exposure to ionizing radiation (U.S. Pat. No. 6,159,443). Peptides within fibrinogen that bind to the radiation-induced $\alpha_{2b}\beta_3$ receptor include HHLGGAKQAGDV (SEQ ID NO:16) and the RGD peptide (Hallahan et al., 2001a).

The present invention includes a study of the targeting activity of $\alpha_{2b}\beta_3$ ligands in tumor-bearing subjects. Example 1 describes x-ray-guided drug delivery in animal models using ligand-conjugated liposomes and microspheres. Clinical trials using a radiolabeled $\alpha_{2b}\beta_3$ ligand support the feasibility of x-ray-guided drug delivery in humans, as described in Example 2. See also Hallahan et al. (2001a) *J Control Release* 74:183-191.

Despite the successes of x-ray-guided drug delivery using $\alpha_{2b}\beta_3$ ligands in experimental models, the clinical application of this approach is limited by nonspecific binding of the targeting ligand at sites other than the tumor (Hallahan et al., 2001b). In addition, previous observations of radiation-inducible molecules have employed radiation doses that are sufficient to limit blood flow, as described in Example 3. Thus, ligands are sought that demonstrate improved tumor specificity and binding to target molecules induced by reduced radiation doses.

III. Identification of Ligands that Bind Irradiated Tumors

Approaches for optimizing peptide binding affinity and specificity have included modification of peptide conformation and addition of flanking amino acids to extend the minimal binding motif. For example, amino acids C-terminal to the RGD sequence are differentially conserved in RGD-containing ligands, and this variation correlates with differences in binding specificity (Cheng et al., 1994; Koivunen et al., 1994). Similarly, cyclization of a prototype RGD peptide to restrict its conformational flexibility improved interaction of the peptide with the vitronectin receptor, yet nearly abolished interaction with the fibronectin receptor (Pierschbacher & Ruoslahti, 1987).

Despite conservation of binding motifs among ligands that bind irradiated tumors and recognition of factors that can influence ligand binding, design of peptide sequences for improved targeting activity is yet unpredictable. Approaches for identifying such peptides have therefore relied on high volume screening methods to select effective motifs from peptide libraries (Koivunen et al., 1993; Healy et al., 1995). However, the utility of in vitro-selected peptides is unpredictable in so far as peptide binding properties are not consistently recapitulated in vivo. To obviate these challenges, the present invention provides a method for in vivo selection of targeting ligands, described further herein below.

Using the in vivo selection method disclosed herein, novel targeting ligands were identified that can be used for x-ray-guided drug delivery. Representative peptide ligands are set forth as SEQ ID NOs:1-13. Representative antibody ligands are set forth as SEQ ID NOs:18 and 20. The novel ligands display improved specificity of binding to irradiated tumors and are effective for targeting using low dose irradiation. The disclosed targeting ligands also offer benefits including moderate cost of preparation and ease of handling.

III.A. Libraries

As used herein, the term "library" means a collection of molecules. A library can contain a few or a large number of different molecules, varying from about ten molecules to several billion molecules or more. A molecule can comprise a naturally occurring molecule, or a synthetic molecule, which is not found in nature. Optionally, as described further herein below, a plurality of different libraries can be employed simultaneously for in vivo panning.

Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168,912 and 5,738,996), a library of antibodies or antibody fragments (U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to an irradiated tumor (e.g., U.S. Pat. Nos. 5,948,635, 5,747,334, and 5,498,538).

The molecules of a library can be produced in vitro, or they can be synthesized in vivo, for example by expression of a molecule in vivo. Also, the molecules of a library can be displayed on any relevant support, for example, on bacterial pili (Lu et al., 1995) or on phage (Smith, 1985).

A library can comprise a random collection of molecules. Alternatively, a library can comprise a collection of molecules having a bias for a particular sequence, structure, or conformation. See e.g., U.S. Pat. Nos. 5,264,563 and 5,824,483. Methods for preparing libraries containing diverse populations of various types of molecules are known in the art, for example as described in U.S. patents cited herein above. Numerous libraries are also commercially available.

In one embodiment of the invention, a peptide library can be used to perform the disclosed in vivo panning methods. In one example, a peptide library comprises peptides comprising three or more amino acids, in another example at least five, six, seven, or eight amino acids, in another example up to 50 amino acids or 100 amino acids, and in yet another example up to about 200 to 300 amino acids.

The peptides can be linear, branched, or cyclic, and can include nonpeptidyl moieties. The peptides can comprise naturally occurring amino acids, synthetic amino acids, genetically encoded amino acids, non-genetically encoded amino acids, and combinations thereof.

A biased peptide library can also be used, a biased library comprising peptides wherein one or more (but not all) residues of the peptides are constant. For example, an internal residue can be constant, so that the peptide sequence is represented as:

where $Xaa_1$ and $Xaa_2$ are any amino acid, or any amino acid except cysteine, wherein $Xaa_1$ and $Xaa_2$ are the same or different amino acids, m and n indicate a number Xaa residues, wherein m and n are independently chosen from the range of 2 residues to 20 residues, more preferably m and n are chosen from the range of 4 residues to 9 residues, and AA is the same amino acid for all peptides in the library. In one example, AA is located at or near the center of the peptide. More specifically, in one example m and n are not different by more than 2 residues; in another example m and n are equal.

The most preferred libraries are those in which AA is tryptophan, proline, or tyrosine. Second most preferred at those in which AA is phenylalanine, histidine, arginine, aspartate, leucine, or isoleucine. Third most preferred are those in which AA is asparagine, serine, alanine, or methionine. The least preferred libraries are those in which AA is cysteine or glycine.

A biased library used for in vivo panning also includes a library comprising molecules previously selected by in vitro panning methods. See Example 8.

In a preferred embodiment of the invention, the method for in vivo panning is performed using a phage peptide library. Phage display is a method to discover peptide ligands while minimizing and optimizing the structure and function of proteins. Phage are used as a scaffold to display recombinant libraries of peptides and provide a means to recover and amplify the peptides that bind to putative receptor molecules in vivo. In vivo phage selection simultaneously provides positive and subtractive screens based on the spatial separation of normal tissues and tumors. Phage that specifically bind the vasculature of normal tissues are removed while specific phage that bind target molecules present in irradiated tumors are enriched through serial rounds of biopanning.

The T7 phage has an icosahedral capsid made of 415 proteins encoded by gene 10 during its lytic phase. The T7 phage display system has the capacity to display peptides up to 15 amino acids in size at a high copy number (415 per phage). Unlike filamentous phage display systems, peptides displayed on the surface of T7 phage are not capable of peptide secretion. T7 phage also replicate more rapidly and are extremely robust when compared to other phage. The stability allows for biopanning selection procedures that require persistent phage infectivity. Accordingly, the use of T7-based phage display is an aspect of a preferred embodiment of the present invention. Example 4 describes a representative method for preparation of a T7 phage peptide library that can be used to perform the in vivo panning methods disclosed herein.

A phage peptide library to be used in accordance with the panning methods of the present invention can also be constructed in a filamentous phage, for example M13 or M13-derived phage. Preferably, the encoded antibodies are displayed at the exterior surface of the phage, for example by fusion to M13 vital protein 8. Methods for preparing M13 libraries can be found in Sambrook & Russell (2001) *Molecular Cloning: A Laboratory Manual,* 3rd ed. Cold Spring Harbor Laboratory Press, Cold Spring Harbor, N.Y., among other places.

In another preferred embodiment of the invention, the method for in vivo panning is performed using a phage antibody library, as described in Example 8. Such a library can be constructed, for example, in M13 or M13-derived phage. See e.g., U.S. Pat. Nos. 6,225,447; 5,580,717; 5,702,892.

III.B. In Vivo Panning for Ligands that Bind Irradiated Tumors

The present invention provides a method for in vivo panning for ligands that bind irradiated tumors. As used herein, the term "in vivo panning" refers to a method of screening a library for selection of a ligand that homes to an irradiated tumor.

The term "in vivo", as used herein to describe methods of panning or ligand selection, refers to contacting of one or more ligands to endogenous candidate target molecules, wherein the candidate target molecules are naturally present in a subject or a tumor biopsy from a subject, and the contacting occurs in the subject or in the biopsied tumor. By contrast, "in vitro" panning refers to contacting a library of candidate ligands with one or more isolated or recombinantly produced target molecules.

Thus, a method for in vivo panning as disclosed herein includes the steps of (a) exposing a tumor to ionizing radiation; (b) administering to a subject a library of diverse molecules; (c) procuring the tumor or fraction thereof; and (d) isolating one or more molecules of the library of diverse molecules from the tumor, whereby a molecule that binds an irradiated tumor is identified. Each step of the method can be sequentially repeated to facilitate ligand selection.

The term "administering to a subject", when used to describe provision of a library of molecules, is used in its broadest sense to mean that the library is delivered to the irradiated tumor. For example, a library can be provided to the circulation of the subject by injection or cannulization such that the molecules can pass through the tumor.

Alternatively or in addition, a library can be administered to an isolated tumor or tumor biopsy. Thus, a method for in vivo panning can also comprise: (a) exposing a tumor and a control tissue to ionizing radiation; (b) administering to the tumor and to the control tissue a library of diverse molecules; (c) detecting one or more molecules of the library that bind to the tumor and that substantially lack binding to the control tissue, whereby a molecule that binds an irradiated tumor is identified.

The in vivo panning methods of the present invention can further comprise administering the library to isolated tumor cells or to isolated proteins prior to administering the library to a subject or to a tumor. For example, in vitro panning methods can be performed to select ligands that bind to particular tumor neoantigens, followed by performance of the in vivo panning methods as disclosed herein.

In a preferred embodiment of the invention, the radiation treatment comprises administration of less than about 2 Gy ionizing radiation. In another preferred embodiment, the radiation treatment comprises at least about 2 Gy ionizing radiation, optionally about 2 Gy to about 3 Gy ionizing radiation, or about 2 Gy to about 6 Gy ionizing radiation. In an alternative preferred embodiment, radiation treatment comprises about 10 Gy to about 20 Gy ionizing radiation.

The methods of the present invention can be performed using any tumor-bearing subject or any subject suspected of having a tumor. Preferably a subject is a warm-blooded vertebrate, more preferably a mammal, and even more preferably a human.

In one embodiment of the invention, a library is administered to a tumor-bearing human subject following irradiation of the tumor. Methods and appropriate doses for administration of a library to a human subject are described in PCT International Publication No. WO 01/09611.

Example 5 describes a representative procedure for in vivo panning of phage-displayed peptide ligands that bind to irradiated tumor vessels in accordance with the present invention.

Briefly, peptide binding was studied in tumor blood vessels of 2 distinct tumor models: (1) GL261 glioma, and (2) Lewis lung carcinoma. Tumors were irradiated with 3 Gy to facilitate identification of peptide sequences that bind tumors exposed to a minimal dose of ionizing radiation. Phage were administered by tail vein injection into tumor bearing mice following irradiation. Phage were recovered from the tumor thereafter. Following multiple rounds of sequential in vivo binding to irradiated tumors, phage were recovered and individual phage were randomly picked and sequenced. Recovered phage were additionally tested for targeting activity in an animal model of melanoma, as described in Example 6.

Example 8 describes a representative procedure for in vivo panning of phage-displayed ligands comprising single chain antibodies. The library used for in vivo panning was a biased library in that a pool of antibody ligands that bind to radiation-induced antigens were pre-selected in vitro.

III.C. Recovery of Targeting Ligands

Methods for identifying targeting ligands that bind an irradiated tumor are selected based on one or more characteristics common to the molecules present in the library. For example, mass spectrometry and/or gas chromatography can be used to resolve molecules that home to an irradiated tumor. Thus, where a library comprises diverse molecules based generally on the structure of an organic molecule, determining the presence of a parent peak for the particular molecule can identify a ligand that binds a radiation-induced target molecule.

If desired, a molecule can be linked to a tag, which can facilitate recovery or identification of the molecule. A representative tag is an oligonucleotide or a small molecule such as biotin. See e.g., Brenner & Lerner (1992) *Proc Natl Acad Sci USA* 89:5381-5383 and U.S. Pat. No. 6,068,829. In addition, a tag can be a support or surface to which a molecule can be attached. For example, a support can be a biological tag such as a virus or virus-like particle such as a bacteriophage ("phage"); a bacterium; or a eukaryotic cell such as yeast, an insect cell, or a mammalian cell (e.g., an endothelial progenitor cell or a leukocyte); or can be a physical tag such as a liposome or a microbead. A support should preferably have a diameter less than about 10 μm to about 50 μm in its shortest dimension, such that the support can pass relatively unhindered through the capillary beds present in the subject and not occlude circulation. In addition, a support can be nontoxic and biodegradable, particularly where the subject used for in vivo panning is not sacrificed for isolation of library molecules from the tumor. Where a molecule is linked to a support, the part of the molecule suspected of being able to interact with a target in a cell in the subject is preferably positioned so as be able to participate in the interaction.

III.D. Peptide Ligands

A targeting peptide of the present invention can be subject to various changes, substitutions, insertions, and deletions where such changes provide for certain advantages in its use. Thus, the term "peptide" encompasses any of a variety of forms of peptide derivatives, that include amides, conjugates with proteins, cyclized peptides, polymerized peptides, conservatively substituted variants, analogs, fragments, peptoids, chemically modified peptides, and peptide mimetics. The terms "targeting peptide" or "peptide ligand" each refer to a peptide as defined herein above that binds to an irradiated tumor.

Peptides of the invention can comprise naturally occurring amino acids, synthetic amino acids, genetically encoded amino acids, non-genetically encoded amino acids, and combinations thereof. Peptides can include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence to a sequence of a reference ligand of radiation inducible target in which one or more residues have been conservatively substituted with a functionally similar residue and which displays the targeting activity as described herein. The phrase "conservatively substituted variant" also includes peptides wherein a residue is replaced with a chemically derivatized residue, provided that the resulting peptide displays targeting activity as disclosed herein.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the present invention also include peptides comprising one or more additions and/or deletions or residues relative to the sequence of a peptide whose sequence is disclosed herein, so long as the requisite targeting activity of the peptide is maintained. The term "fragment" refers to a peptide comprising an amino acid residue sequence shorter than that of a peptide disclosed herein.

Additional residues can also be added at either terminus of a peptide for the purpose of providing a "linker" by which the peptides of the present invention can be conveniently affixed to a label or solid matrix, or carrier. Amino acid residue linkers are usually at least one residue and can be 40 or more residues, more often 1 to 10 residues, but do alone not constitute radiation inducible target ligands. Typical amino acid residues used for linking are tyrosine, cysteine, lysine, glutamic and aspartic acid, or the like. In addition, a peptide can be modified by terminal-$NH_2$ acylation (e.g., acetylation, or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half life of the peptides in solutions, particularly biological fluids where proteases can be present.

Peptide cyclization is also a useful terminal modification, and is particularly preferred also because of the stable structures formed by cyclization and in view of the biological activities observed for such cyclic peptides as described herein. An exemplary method for cyclizing peptides is described by Schneider & Eberle (1993) *Peptides, 1992: proceedings of the Twenty-Second European Peptide Symposium*, Sep. 13-19, 1992, Interlaken, Switzerland, Escom, Leiden. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxyl termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al. (1993) *J Med Chem* 36:166-172; Garbay-Jaureguiberry et al. (1992) *Int J Pept Protein Res* 39:523-527; Tung et al. (1992) *Pept Res* 5:115-118; Urge et al. (1992) *Carbohydr Res* 235:83-93; Pavone et al. (1993) *Int J Pept Protein Res* 41:15-20.

Peptides of the present invention, including peptoids, can be synthesized by any of the techniques that are known to those skilled in the art of peptide synthesis. Synthetic chemistry techniques, such as a solid-phase Merrifield-type synthesis, are preferred for reasons of purity, antigenic specificity, freedom from undesired side products, ease of production and the like. A summary of representative techniques can be found in Stewart & Young (1969) *Solid Phase Peptide Synthesis*. Freeman, San Francisco; Merrifield (1969) *Adv Enzymol Relat Areas Mol Biol* 32:221-296; Fields & Noble (1990) *Int J Pept Protein Res* 35:161-214; and Bodanszky (1993) *Principles of Peptide Synthesis*. 2nd rev. ed. Springer-Verlag, Berlin; New York. Solid phase synthesis techniques can be found in Andersson et al. (2000) *Biopolymers* 55:227-250, references cited therein, and in U.S. Pat. Nos. 6,015,561, 6,015,881, 6,031,071, and 4,244,946. Peptide synthesis in solution is described by Schröder & Lübke (1965) The Peptides. Academic Press, New York. Appropriate protective groups usable in such synthesis are described in the above texts and in McOmie (1973) *Protective Groups in Organic Chemistry*. Plenum Press, London, New York. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif. and PeptidoGenics of Livermore, Calif.).

The term "peptide mimetic" as used herein refers to a ligand that mimics the biological activity of a reference peptide, by substantially duplicating the targeting activity of the reference peptide, but it is not a peptide or peptoid. Preferably, a peptide mimetic has a molecular weight of less than about 700 daltons.

A peptide mimetic can be designed by: (a) identifying the pharmacophoric groups responsible for the targeting activity of a peptide; (b) determining the spatial arrangements of the pharmacophoric groups in the active conformation of the peptide; and (c) selecting a pharmaceutically acceptable template upon which to mount the pharmacophoric groups in a manner that allows them to retain their spatial arrangement in the active conformation of the peptide. For identification of pharmacophoric groups responsible for targeting activity, mutant variants of the peptide can be prepared and assayed for targeting activity. Alternatively or in addition, the three-dimensional structure of a complex of the peptide and its target molecule can be examined for evidence of interactions, for example the fit of a peptide side chain into a cleft of the target molecule, potential sites for hydrogen bonding, etc. The spatial arrangements of the pharmacophoric groups can be determined by NMR spectroscopy or X-ray diffraction studies. An initial three-dimensional model can be refined by energy minimization and molecular dynamics simulation. A template for modeling can be selected by reference to a template database and will typically allow the mounting of 2-8 pharmacophores. A peptide mimetic is identified wherein addition of the pharmacophoric groups to the template maintains their spatial arrangement as in the peptide.

A peptide mimetic can also be identified by assigning a hashed bitmap structural fingerprint to the peptide based on its chemical structure, and determining the similarity of that fingerprint to that of each compound in a broad chemical database. The fingerprints can be determined using fingerprinting software commercially distributed for that purpose by Daylight Chemical Information Systems, Inc. (Mission Viejo, Calif.) according to the vendor's instructions. Representative databases include but are not limited to SPREI'95 (InfoChem GmbH of München, Germany), Index Chemicus (ISI of Philadelphia, Pa.), World Drug Index (Derwent of London, United Kingdom), TSCA93 (United States Envrionmental Protection Agency), MedChem (Biobyte of Claremont, Calif.), Maybridge Organic Chemical Catalog (Maybridge of Cornwall, England), Available Chemicals Directory (MDL Information Systems of San Leandro, Calif.), NCI96 (United States National Cancer Institute), Asinex Catalog of Organic Compounds (Asinex Ltd. of Moscow, Russia), and NP (InterBioScreen Ltd. of Moscow, Russia). A peptide mimetic of a reference peptide is selected as comprising a fingerprint with a similarity (Tanamoto coefficient) of at least 0.85 relative to the fingerprint of the reference peptide. Such peptide mimetics can be tested for bonding to an irradiated tumor using the methods disclosed herein.

Additional techniques for the design and preparation of peptide mimetics can be found in U.S. Pat. Nos. 5,811,392; 5,811,512; 5,578,629; 5,817,879; 5,817,757; and 5,811,515.

Any peptide or peptide mimetic of the present invention can be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

III.E. Antibody Ligands

An targeting antibody or the present invention comprises an antibody identified by the in vivo panning methods disclosed herein. Preferably, an antibody targeting ligand comprises: (a) a polypeptide comprising an amino acid sequence of SEQ ID NO:18 or 20; (b) a polypeptide substantially identical to SEQ ID NO:18 or 20; (c) a polypeptide encoded by SEQ ID NO:17 or 19; or (d) a polypeptide substantially identical to SEQ ID NO:17 or 19. Thus, the present invention also provides an isolated nucleic acid that encodes an antibody targeting ligand comprising: (a) a nucleic acid molecule comprising the nucleotide sequence of SEQ ID NO:17 or 19; or (b) a nucleic acid molecule substantially identical to SEQ ID NO:17 or 19.

The term "isolated", as used in the context of a nucleic acid or polypeptide, indicates that the nucleic acid or polypeptide exists apart from its native environment and is not a product of nature. An isolated nucleic acid or polypeptide can exist in a purified form or can exist in a non-native environment such as a transgenic host cell.

Nucleic Acids Encoding Targeting Antibodies. The terms "nucleic acid molecule" or "nucleic acid" each refer to deoxyribonucleotides or ribonucleotides and polymers thereof in single-stranded or double-stranded. Unless specifically limited, the term encompasses nucleic acids containing known analogues of natural nucleotides that have similar properties as the reference natural nucleic acid. The terms "nucleic acid molecule" or "nucleic acid" can also be used in place of "gene", "cDNA", or "mRNA". Nucleic acids can be synthesized, or can be derived from any biological source, including any organism.

The term "substantially identical", as used herein to describe a degree of similarity between nucleotide sequences, refers to two or more sequences that have at least about least 60%, preferably at least about 70%, more preferably at least about 80%, more preferably about 90% to about 99%, still more preferably about 95% to about 99%, and most preferably about 99% nucleotide identity, as measured using one of the following sequence comparison algorithms (described herein below) or by visual inspection. Preferably, the substantial identity exists in nucleotide sequences of at least about 100 residues, more preferably in nucleotide sequences of at least about 150 residues, and most preferably in nucleotide sequences comprising a full length coding sequence.

Thus, substantially identical sequences can comprise mutagenized sequences, including sequences comprising silent mutations, or variably synthesized sequences. A mutation or variant sequence can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

A preferred nucleotide sequence employed for hybridization studies or assays includes probe sequences that are complementary to or mimic at least an about 14 to 40 nucleotide sequence of a nucleic acid molecule of the present invention. For this purpose, a probe comprises a region of the nucleic acid molecule other than a sequence encoding a common immunoglobulin region. Thus, a probe preferably comprises a sequence encoding a domain of the antibody that comprises an antigen binding site. Preferably, probes comprise 14 to 20 nucleotides, or even longer where desired, such as 30, 40, 50, 60, 100, 200, 300 nucleotides or up to the full length of a region of SEQ ID NO:17 or 19 that encodes an antigen binding site. Such fragments can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, part I chapter 2, Elsevier, New York, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds (1989) *Molecular Cloning: A Laboratory Manual*, Cold Spring Harbor Laboratory Press, Cold Spring Harbor, N.Y. for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1 M $Na^+$ ion, typically about 0.01 to 1 M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the present invention: a probe nucleotide sequence preferably hybridizes to a target nucleotide sequence in 7% sodium dodecyl sulfate (SDS), 0.5M NaPO$_4$, 1 mM EDTA at 50° C. followed by washing in 2×SSC, 0.1% SDS at 50° C.; more preferably, a probe and target sequence hybridize in 7% sodium dodecyl sulfate (SDS), 0.5M NaPO$_4$, 1 mM EDTA at 50° C. followed by washing in 1×SSC, 0.1% SDS at 50° C.; more preferably, a probe and target sequence hybridize in 7% sodium dodecyl sulfate (SDS), 0.5M NaPO$_4$, 1 mM EDTA at 50° C. followed by washing in 0.5×SSC, 0.1% SDS at 50° C.; more preferably, a probe and target sequence hybridize in 7% sodium dodecyl sulfate (SDS), 0.5M NaPO$_4$, 1 mM EDTA at 50° C. followed by washing in 0.1×SSC, 0.1% SDS at 50° C.; more preferably, a probe and target sequence hybridize in 7% sodium dodecyl sulfate (SDS), 0.5M NaPO$_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Batzer et al. (1991) *Nucleic Acids Res* 19:5081; Ohtsuka et al. (1985) *J Biol Chem* 260:2605-2608; Rossolini et al. (1994) *Mol Cell Probes* 8:91-98

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising about 8 or more deoxyribonucleotides or ribonucleotides, preferably 10-20 nucleotides, and more preferably 20-30 nucleotides of a selected nucleic acid molecule. The primers of the invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

Nucleic acids of the present invention can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook et al. (eds.) (1989) *Molecular Cloning: A Laboratory Manual*. Cold Spring Harbor Laboratory Press, Cold Spring Harbor; Silhavy et al. (1984) *Experiments with Gene Fusions*. Cold Spring Harbor Laboratory, Cold Spring Harbor, N.Y.; Glover & Hames (1995) *DNA Cloning: A Practical Approach*, 2nd ed. IRL Press at Oxford University Press, Oxford/New York; Ausubel (ed.) (1995) *Short Protocols in Molecular Biology*, 3rd ed. Wiley, New York.

Single Chain Antibody Polypeptides. The term "substantially identical", as used herein to describe a level of similarity between a polypeptide comprising an antibody targeting ligand and a polypeptide to SCN1A, refers to a sequence having at least about 45%, more preferably at least about 50%, still more preferably at least about 60%, still more preferably at least about 70%, still more preferably at least about 80%, still more preferably at least about 90%, still more preferably at least about 95%, and still more preferably at least about 99% sequence identity to SEQ ID NO:17 or 19, when compared over the full length of the single chain polypeptide. The term "full length", as used herein to describe an antibody targeting ligand, comprises an amino acid sequence having 254 amino acids. Methods for determining percent identity are defined herein below.

Substantially identical polypeptides also encompass two or more polypeptides sharing a conserved three-dimensional structure. Computational methods can be used to compare structural representations, and structural models can be generated and easily tuned to identify similarities around important active sites or ligand binding sites. See Saqi et al. (1999) *Bioinformatics* 15:521-522; Barton (1998) *Acta Crystallogr D Biol Crystallogr* 54:1139-1146; Henikoff et al. (2000) *Electrophoresis* 21:1700-1706; Huang et al. (2000) *Pac Symp Biocomput*:230-241.

Substantially identical proteins also include proteins comprising an amino acid sequence comprising amino acids that are functionally equivalent to amino acids of SEQ ID NOs:18 and 20. The term "functionally equivalent" in the context of amino acid sequences is known in the art and is based on the relative similarity of the amino acid side-chain substituents. See Henikoff & Henikoff (2000) *Adv Protein Chem* 54:73-97. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

The term "substantially identical" also encompasses polypeptides that are biologically functional equivalents. The term "functional", as used herein to describe polypeptides comprising antibody targeting ligands, refers two or more antibodies that are immunoreactive with a same radiation-induced target molecule. Preferably, the two or more antibodies specifically bind a same target molecule and substantially lack binding to a control antigen.

The term "specifically binds", when used to describe binding of an antibody to a target molecule, refers to binding to a target molecule in a heterogeneous mixture of other polypeptides.

The phases "substantially lack binding" or "substantially no binding", as used herein to describe binding of an antibody to a control polypeptide or sample, refers to a level of binding that encompasses non-specific or background binding, but does not include specific binding.

Techniques for detecting antibody-target molecule complexes are known in the art and include but are not limited to centrifugation, affinity chromatography and other immunochemical methods. Preferably, an antibody-target molecule complex can be detected following administration of an antibody to a subject as described in Examples 6 and 7. Also preferably, an antibody-target molecule complex can be detected in vivo by performing radiation-guided drug delivery, wherein the drug comprises a targeting antibody of SEQ ID NO:18 or 20 and a detectable label, as described in Examples 1 and 2. See also, Manson (1992) *Immunochemical Protocols*. Humana Press, Totowa, N.J.; Ishikawa (1999) *Ultrasensitive and Rapid Enzyme Immunoassay*. Elsevier, Amsterdam; New York; Law (1996) *Immunoassay: A Practical Guide*.

The present invention also provides functional fragments of a antibody targeting polypeptide. Such functional portion need not comprise all or substantially all of the amino acid sequence of SEQ ID NO:18 or 20.

The present invention also includes functional polypeptide sequences that are longer sequences than that of SEQ ID NO:18 or 20. For example, one or more amino acids can be added to the N-terminus or C-terminus of a antibody targeting ligand. Methods of preparing such proteins are known in the art.

Isolated polypeptides and recombinantly produced polypeptides can be purified and characterized using a variety of standard techniques that are known to the skilled artisan. See e.g., Schröder & Lübke (1965) *The Peptides*. Academic Press, New York; Schneider & Eberle (1993) *Peptides, 1992: Proceedings of the Twenty-Second European Peptide Symposium*, Sep. 13-19, 1992, Interlaken, Switzerland. Escom, Leiden; Bodanszky (1993) *Principles of Peptide Synthesis*, 2nd rev. ed. Springer-Verlag, Berlin; New York; Ausubel (ed.) (1995) *Short Protocols in Molecular Biology*, 3rd ed. Wiley, New York.

Nucleotide and Amino Acid Sequence Comparisons. The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman (1981) *Adv Appl Math* 2:482-489, by the homology alignment algorithm of Needleman & Wunsch (1970) *J Mol Biol* 48:443-453, by the search for similarity method of Pearson & Lipman (1988) *Proc Natl Acad Sci USA* 85:2444-2448, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel (ed.) (1995) *Short Protocols in Molecular Biology*, 3rd ed. Wiley, New York.

A preferred algorithm for determining percent sequence identity and sequence similarity is the BLAST algorithm, which is described in Altschul et al. (1990) *J Mol Biol* 215:403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff (1992) *Proc Natl Acad Sci U S A* 89:10915-10919.

In addition to calculating percent sequence identity, the BLAST algorithm also performs a statistical analysis of the similarity between two sequences. See e.g., Karlin & Altschul (1993) *Proc Natl Acad Sci USA* 90:5873-5877. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

IV. Tumor Diagnosis, Treatment, and Imaging

The present invention further provides methods and compositions for x-ray guided drug delivery to a tumor in a subject. The term "drug" as used herein refers to any substance having biological or detectable activity. Thus, the term "drug" includes a pharmaceutical agent, a diagnostic agent, or a combination thereof. The term "drug" also includes any substance that is desirably delivered to a tumor.

Thus, in one embodiment of the invention, a composition is prepared, the composition comprising a targeting ligand as disclosed herein and a diagnostic agent. The composition can be used for the detection of a tumor in a subject by: (a) exposing a suspected tumor to ionizing radiation; (b) administering to the subject a targeting ligand of the invention, wherein the ligand comprises a detectable label; and (c) detecting the detectable label, whereby a tumor is diagnosed. Alternatively, a method for detecting a tumor can comprise: (a) exposing a suspected tumor to ionizing radiation; (b) biopsing a suspected tumor; (c) contacting a targeting ligand of the invention with the suspected tumor in vitro, wherein the ligand comprises a detectable label; and (d) detecting the detectable label, whereby a tumor is diagnosed.

A therapeutic composition of the present invention can comprise one or more targeting ligands and a therapeutic agent, such that the therapeutic agent can be selectively targeted to an irradiated tumor. The one or more targeting ligands can comprise ligands having diverse molecular features. For example, one or more targeting ligands can comprise both peptide and antibody targeting ligands.

Optionally, a therapeutic composition can additionally comprise a detectable label, preferably a label that can be detected in vivo. The biodistribution of the therapeutic composition so prepared can be monitored following administration to a subject.

Methods for preparation, labeling, and x-ray guided drug delivery using targeting ligands of the present invention are described further herein below. See also Examples 1 and 2.

IV.A. Therapeutic Agents

The novel targeting ligands disclosed here are used to target a therapeutic agent to an irradiated tumor. Representative therapeutic agents include but are not limited to a nucleic acid (e.g., a therapeutic gene) and a small molecule. In a preferred embodiment of the invention, an inactive drug is administered, which is subsequently activated by irradiation (Hallahan et al., 1995b). For example, therapeutic gene expression can be regulated by a radiation-inducible promoter (Hallahan et a., 1995b).

Therapeutic Genes. Angiogenesis and suppressed immune response play a central role in the pathogenesis of malignant disease and tumor growth, invasion, and metastasis. Thus, a preferred therapeutic gene encodes a polypeptide having an ability to induce an immune response and/or an anti-angiogenic response in vivo.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), Representative therapeutic proteins with immunostimulatory effects include but are not limited to cytokines (e.g., IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule (2000) *Hum Gene Ther* 11:797-806; Mackensen et al. (1997) *Cytokine Growth Factor Rev* 8:119-128; Walther & Stein (1999) *Mol Biotechnol* 13:21-28; and references cited therein.

The term "angiogenesis" refers to the process by which new blood vessels are formed. The term "anti-angiogenic response" and "anti-angiogenic activity" as used herein, each refer to a biological process wherein the formation of new blood vessels is inhibited.

Representative proteins with anti-angiogenic activities that can be used in accordance with the present invention include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et a., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991).

A gene therapy construct used in accordance with the methods of the present invention can also encode a therapeutic gene that displays both immunostimulatory and anti-angiogenic activities, for example, IL12 (See Dias et al. (1998) *Int J Cancer* 75:151-157; and references cited herein below), interferon-α (O'Byrne et al., 2000), and references cited therein), or a chemokine (Nomura & Hasegawa, 2000, and references cited therein). In addition, a gene therapy construct can encode a gene product with immunostimulatory activity and a gene product having anti-angiogenic activity. See e.g. Narvaiza et al. (2000) *J Immunol* 164:3112-3122.

Additional compositions useful for cancer therapy include but are not limited to genes encoding tumor suppressor gene products/antigens, antimetabolites, suicide gene products, and combinations thereof. See Kirk & Mule (2000) *Hum Gene Ther* 11:797-806; Mackensen et al. (1997) *Cytokine Growth Factor Rev* 8:119-128; Walther & Stein (1999) *Mol Biotechnol* 13:21-28; and references cited therein.

Therapeutic Compounds. In accordance with the methods of the present invention, a therapeutic agent can also comprise a cytotoxic agent, a chemotherapeutic agent, a radionuclide, or any other anti-tumor molecule. Studies using ligand/drug conjugates have demonstrated that a chemotherapeutic agent can be linked to a ligand to produce a conjugate that maintains the binding specificity of the ligand and the therapeutic function of the agent. For example, doxorubicin has been linked to antibodies or peptides and the ligand/doxorubicin conjugates display cytotoxic activity (Shih et al., 1994; Lau et al., 1995; Sivam et al., 1995), PCT International Publication No. WO 98/10795). Similarly, other anthracyclines, including idarubicin and daunorubocin, have been chemically conjugated to antibodies, which have facilitated delivery of effective doses of the agents to tumors (Aboud-Pirak et al., 1989; Rowland et al., 1993). Other chemotherapeutic agents include cis-platinum (Schechter et al., 1991), methotrexate (Shawler et al., 1988; Fitzpatrick & Garnett, 1995) and mitomycin-C (Dillman et al., 1989).

In another embodiment of the invention, a therapeutic agent comprises a radionuclide. Radionuclides can be effectively conjugated to antibodies (Hartmann et al., 1994; Buchsbaum et al., 1995), small molecule ligands (Wilbur, 1992; Fjalling et al., 1996), and peptides (Boerman et al., 2000; Krenning & de Jong, 2000; Kwekkeboom et al., 2000; Virgolini et al., 2001, and references cited therein), such that administration of the conjugated radionuclide promotes tumor regression. Representative therapeutic radionuclides and methods for preparing a radionuclide-labeled agent are described further herein below under the heading Scinitgraphic Imaging. For therapeutic methods of the present invention, a preferred radionuclide comprises $^{131}$I.

Additional anti-tumor agents that can be conjugated to the targeting ligands disclosed herein and used in accordance with the therapeutic methods of the present invention include but are not limited to alkylating agents such as melphalan and chlorambucil (Smyth et al., 1987; Aboud-Pirak et al., 1989; Rowland et al., 1993), vinca alkaloids such as vindesine and vinblastine (Aboud-Pirak et al., 1989; Starling et al., 1992), antimetabolites such as 5-fluorouracil, 5-fluorouridine and derivatives thereof (Krauer et al., 1992; Henn et al., 1993).

IV.B. Preparation of a Therapeutic and/or Diagnostic Composition

The present invention also provides a method for preparing a composition for x-ray-guided drug delivery. The method comprises: (a) performing in vivo panning, whereby a ligand that binds a radiation-inducible tumor molecule is identified; and (b) conjugating the ligand to a drug, whereby a composition for x-ray-guided drug delivery is prepared. A drug can further comprise a drug carrier and can be formulated in any manner suitable for administration to a subject. In a preferred embodiment of the invention, the method employs a targeting ligand identified by in vivo panning comprising any one of SEQ ID NOs:1-13,18, and 20.

Drug Carriers. The compositions of the present invention can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan, 2001a; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997 and U.S. Pat. Nos. 4,551,482, 5,714,166, 5,510,103, 5,490,840, and 5,855,900), and a polysome (U.S. Pat. No. 5,922,545).

Conjugation of Targeting Ligands. Antibodies, peptides, or other ligands can be coupled to drugs or drug carriers using methods known in the art, including but not limited to carbodiimide conjugation, esterification, sodium periodate oxidation followed by reductive alkylation, and glutaraldehyde crosslinking. See Goldman et al. (1997) *Cancer Res* 57:1447-1451; Cheng (1996) *Hum Gene Ther* 7:275-282; Neri et al. (1997) *Nat Biotechnol* 15:1271-1275; Nabel (1997), *Current Protocols in Human Genetics*. John Wiley & Sons, New York, Vol. on CD-ROM; Park et al. (1997) *Adv Pharmacol* 40:399-435; Pasqualini et al. (1997) *Nat Biotechnol* 15:542-546; Bauminger & Wilchek (1980) *Methods Enzymol* 70:151-159; U.S. Pat. No. 6,071,890; and European Patent No. 0 439 095.

In addition, a targeting peptide or antibody can be recombinantly expressed. For example, a nucleotide sequence encoding a targeting peptide or ligand can be cloned into adenovirus DNA encoding the H1 loop fiber, such that the targeting peptide or ligand is extracellularly presented. An adenovirus vector so prepared can be used for x-ray-guided delivery of a gene therapy construct as disclosed herein. A modified adenovirus vector encoding the RGD peptide was observed to transduce the endothelium in tumor blood vessels.

Formulation. A therapeutic composition, a diagnostic composition, or a combination thereof, of the present invention preferably comprises a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some preferred ingredients are SDS, for example in the range of 0.1 to 10 mg/ml, preferably about 2.0 mg/ml; and/or mannitol or another sugar, for example in the range of 10 to 100 mg/ml, preferably about 30 mg/ml; and/or phosphate-buffered saline (PBS). Any other agents conventional in the art having regard to the type of formulation in question can be used.

The therapeutic regimens and pharmaceutical compositions of the invention can be used with additional adjuvants or biological response modifiers including, but not limited to, the cytokines IFN-α, IFN-γ, IL2, IL4, IL6, TNF, or other cytokine affecting immune cells.

IV.C. Administration

Suitable methods for administration of a therapeutic composition, a diagnostic composition, or combination thereof, of the present invention include but are not limited to intravascular, subcutaneous, or intratumoral administration. Preferably, intravascular administration is employed. For delivery of compositions to pulmonary pathways, compositions can be administered as an aerosol or coarse spray.

For therapeutic applications, a therapeutically effective amount of a composition of the invention is administered to a subject. A "therapeutically effective amount" is an amount of the therapeutic composition sufficient to produce a measurable biological tumor response (e.g., an immunostimulatory, an anti-angiogenic response, a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. Preferably, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the invention is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled antibody prior to imaging, the route of drug administration, the physical condition and prior medical history of the subject, and the size and longevity of the tumor or suspected tumor. Thus, a detectable amount can vary and is preferably tailored to a particular application. After study of the present disclosure, and in particular the Examples, it is within the skill of one in the art to determine such a detectable amount.

IV.D. Radiation Treatment

The disclosed targeting ligands are useful for x-ray guided drug delivery. Targeted drug delivery to a tumor in a subject can be performed by irradiating the tumor prior to, concurrent with, or subsequent to administration of a composition of the present invention. In accordance with the in vivo panning methods for discovery of the targeting ligands, the tumor is preferably irradiated 0 hours to about 24 hours before administration of the composition, and more preferably about 4 hours to about 24 hours before administration of the composition.

Low doses of radiation can be used for selective targeting using the peptide ligands disclosed herein. Preferably, the dose of radiation comprises up to about 2 Gy ionizing radiation. Higher radiation doses can also be used, especially in the case of local radiation treatment as described herein below.

Radiation can be localized to a tumor using conformal irradiation, brachytherapy, or stereotactic irradiation. The threshold dose for inductive changes can thereby be exceeded in the target tissue but avoided in surrounding normal tissues. In this case, dose of at least about 2 Gy ionizing radiation can be used, and more preferably about 10 Gy to about 20 Gy ionizing radiation. For treatment of a subject having two or more tumors, local irradiation enables differential drug administration and/or dose at each of the two or more tumors. Alternatively, whole body irradiation can be used, as permitted by the low doses of radiation required for targeting of ligands disclosed herein. Radiotherapy methods suitable for use in the practice of this invention can be found in Leibel & Phillips (1998) *Textbook of Radiation Oncology*, Saunders, Philadelphia, among other sources.

IV.E. Monitoring Distribution In vivo

In a preferred embodiment of the invention, a diagnostic and/or therapeutic composition for x-ray-guided drug delivery comprises a label that can be detected in vivo. The term "in vivo", as used herein to describe imaging or detection methods, refer to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

The label can be conjugated or otherwise associated with a targeting ligand (e.g., any one of SEQ ID NOs:1-13, 18, 20), a therapeutic, a diagnostic agent, a drug carrier, or combinations thereof. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

Scintigraphic Imaging. Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

A representative method for SPECT imaging is presented in Example 2. Other imaging instruments suitable for practicing the method of the present invention, and instruction for using the same, are readily available from commercial sources. Both PET and SPECT systems are offered by ADAC of Milpitas, Calif. and Siemens of Hoffman Estates, Illinois. Related devices for scintigraphic imaging can also be used, such as a radio-imaging device that includes a plurality of sensors with collimating structures having a common source focus.

When scintigraphic imaging is employed, the detectable label preferably comprises a radionuclide label, more preferably a radionuclide label selected from the group consisting of $^{18}$fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$indium, $^{113}$mindium, $^{99m}$rhenium, $^{105}$rhenium, $^{101}$rhenium, $^{186}$rhenium, $^{188}$rhenium, $^{121}$mtellurium, $^{122m}$tellurium, $^{125m}$tellurium, $^{165}$thulium, $^{167}$thulium, $^{168}$thulium, and nitride or oxide forms derived there from. In a preferred embodiment of the invention, the radionuclide label comprises $^{131}$iodine or $^{99m}$Tc.

Methods for radionuclide-labeling of a molecule so as to be used in accordance with the disclosed methods are known in the art. For example, a targeting molecule can be derivatized so that a radioisotope can be bound directly to it (Yoo et al., 1997). Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (HMPAO) (Chattopadhyay et al., 2001; Sagiuchi et al., 2001; Dewanjee et al., 1994; U.S. Pat. No. 6,024,938). Additional methods can be found in U.S. Pat. No. 6,080,384; Hnatowich et al. (1996) *J Pharmacol Exp Ther* 276:326-334; and Tavitian et al. (1998) *Nat Med* 4:467-471.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI). Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging (fMRI). See Rovaris et al. (2001) *J Neurol Sci* 186 Suppl 1:S3-9; Pomper & Port (2000) *Magn Reson Imaging Clin N Am* 8:691-713; and references cited therein.

Contrast agents for magnetic source imaging include but are not limited to paramagnetic or superparamagnetic ions, iron oxide particles (Weissleder et al., 1992; Shen et al., 1993), and water-soluble contrast agents. Paramagnetic and superparamagnetic ions can be selected from the group of metals including iron, copper, manganese, chromium, erbium, europium, dysprosium, holmium and gadolinium. Preferred metals are iron, manganese and gadolinium; most preferred is gadolinium.

Those skilled in the art of diagnostic labeling recognize that metal ions can be bound by chelating moieties, which in turn can be conjugated to a therapeutic agent in accordance with the methods of the present invention. For example, gadolinium ions are chelated by diethylenetriaminepentaacetic acid (DTPA). Lanthanide ions are chelated by tetraazacyclododocane compounds. See U.S. Pat. Nos. 5,738,837 and 5,707,605. Alternatively, a contrast agent can be carried in a liposome (Schwendener, 1992).

Images derived used a magnetic source can be acquired using, for example, a superconducting quantum interference device magnetometer (SQUID, available with instruction from Quantum Design of San Diego, Calif.). See U.S. Pat. No. 5,738,837.

Ultrasound. Ultrasound imaging can be used to obtain quantitative and structural information of a target tissue, including a tumor. Administration of a contrast agent, such as gas microbubbles, can enhance visualization of the target tissue during an ultrasound examination. Preferably, the contrast agent can be selectively targeted to the target tissue of interest, for example by using a peptide for x-ray guided drug delivery as disclosed herein. Representative agents for providing microbubbles in vivo include but are not limited to gas-filled lipophilic or lipid-based bubbles (e.g., U.S. Pat. Nos. 6,245,318, 6,231,834, 6,221,018, and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the invention include air; nitrogen; oxygen; is carbon dioxide; hydrogen; nitrous oxide; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus are preferred for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

A description of ultrasound equipment and technical methods for acquiring an ultrasound dataset can be found in Coatney (2001) *Ilar J* 42:233-247, Lees (2001) *Semin Ultrasound CT MR* 22:85-105, and references cited therein.

Fluorescent Imaging. Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging. See e.g. Fraser (1996) *Methods Cell Biol* 51:147-160; Ragnarson et al. (1992) *Histochemistry* 97:329-333; and Heredia et al. (1991) *J Neurosci Methods* 36:17-25. Representative labels include but are not limited to carbocyanine and aminostyryl dyes, preferably long chain dialkyl carbocyanines (e.g., DiI, DiO, and DiD available from Molecular Probes Inc. of Eugene, Oreg.) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg.). Preparation of liposomes comprising a targeting ligand and a DiI detectable label are described in Example 1.

A fluorescent label can also comprise sulfonated cyanine dyes, including Cy5.5 and Cy5 (available from Amersham of Arlington Heights, Ill.), IRD41 and IRD700 (available from Li-Cor, Inc. of Lincoln, Nebr.), NIR-1 (available from Dejindo of Kumamoto, Japan), and LaJolla Blue (available from Diatron of Miami, Fla.). See also Licha et al. (2000) *Photochem Photobiol* 72:392-398; Weissleder et al. (1999) *Nat Biotechnol* 17:375-378; and Vinogradov et al. (1996) *Biophys J* 70:1609-1617

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

IV.F. In Vitro Detection

The present invention further provides methods for diagnosing a tumor, wherein a tumor sample or biopsy is evaluated in vitro. In this case, a targeting ligand of the invention comprises a detectable label such as a fluorescent, epitope, or radioactive label, each described briefly herein below.

Fluorescence. Any detectable fluorescent dye can be used, including but not limited to FITC (fluorescein isothiocyanate), FLUOR X™, ALEXA FLUOR®, OREGON GREEN®, TMR (tetramethylrhodamine), ROX (X-rhodamine), TEXAS RED®, BODIPY® 630/650, and Cy5 (available from Amersham Pharmacia Biotech of Piscataway, N.J. or from Molecular Probes Inc. of Eugene, Oreg.).

A fluorescent label can be detected directly using emission and absorbance spectra that are appropriate for the particular label used. Common research equipment has been developed for in vitro detection of fluorescence, including instruments available from GSI Lumonics (Watertown, Mass., United States of America) and Genetic MicroSystems Inc. (Woburn, Mass., United States of America). Most of the commercial systems use some form of scanning technology with photomultiplier tube detection. Criteria for consideration when analyzing fluorescent samples are summarized by Alexay et al. (1996) *The PCT International Society of Optical Engineering* 2705/63.

Detection of an Epitope. If an epitope label has been used, a protein or compound that binds the epitope can be used to detect the epitope. A representative epitope label is biotin, which can be detected by binding of an avidin-conjugated fluorophore, for example avidin-FITC, as described in Example 7. Alternatively, the label can be detected by binding of an avidin-horseradish peroxidase (HRP) streptavidin conjugate, followed by calorimetric detection of an HRP enzymatic product. The production of a calorimetric or luminescent product/conjugate is measurable using a spectrophotometer or luminometer, respectively.

Autoradiographic Detection. In the case of a radioactive label (e.g., $^{131}I$ or $^{99m}Tc$) detection can be accomplished by conventional autoradiography or by using a phosphorimager as is known to one of skill in the art. A preferred autoradiographic method employs photostimulable luminescence imaging plates (Fuji Medical Systems of Stamford, Conn.). Briefly, photostimulable luminescence is the quantity of light emitted from irradiated phosphorous plates following stimulation with a laser during scanning. The luminescent response of the plates is linearly proportional to the activity (Amemiya et al., 1988; Hallahan et al., 2001b).

V. Identification of a Radiation-Induced Target Molecule

Targeting ligands obtained using the methods disclosed herein can be used to identify and/or isolate a target molecule that is recognized by the targeting ligand. Representative methods include affinity chromatography, biotin trapping, and two-hybrid analysis, each described briefly herein below.

Affinity Chromatography. A representative method for identification of a radiation-induced target molecule is affinity chromatography. For example, a targeting ligand as disclosed herein can be linked to a solid support such as a chromatography matrix. A sample derived from an irradiated tumor is prepared according to known methods in the art, and such sample is provided to the column to permit binding of a target molecule. The target molecule, which forms a complex with the targeting ligand, is eluted from the column and collected in a substantially isolated form. The substantially isolated target molecule is then characterized using standard methods in the art. See Deutscher (1990) *Guide to Protein Purification*. Academic Press, San Diego.

Biotin Trapping. A related method employs a biotin-labeled targeting ligand such that a complex comprising the biotin-labeled targeting ligand bound to a target molecule can be purified based on affinity to avidin, which is provided on a support (e.g., beads, a column). A targeting ligand comprising a biotin label can be prepared by any one of several methods, including binding of biotin maleimide [3-(N-maleimidylpropionyl)biocytin] to cysteine residues of a peptide ligand (Tang & Casey, 1999), binding of biotin to a biotin acceptor domain, for example that described in *K. pneumoniae* oxaloacetate decarboxylase, in the presence of biotin ligase (Julien et al., 2000), attachment of biotin amine to reduced sulfhydryl groups (U.S. Pat. No. 5,168,037), and chemical introduction of a biotin group into a nucleic acid ligand, (Carninci et al., 1996). Preferably, a biotin-labeled targeting ligand and the unlabeled same target ligand show substantially similar binding to a target molecule.

Two-Hybrid Analysis. As another example, targeting ligands can be used to identify a target molecule using a two-hybrid assay, for example a yeast two-hybrid or mammalian two-hybrid assay. In one embodiment of the method, a targeting ligand is fused to a DNA binding domain from a transcription factor (this fusion protein is called the "bait"). Representative DNA-binding domains include those derived from GAL4, LEXA, and mutant forms thereof. One or more candidate target molecules is fused to a transactivation domain of a transcription factor (this fusion protein is called the "prey"). Representative transactivation domains include those derived from *E. coli* B42, GAL4 activation domain II, herpes simplex virus VP16, and mutant forms thereof. The fusion proteins can also include a nuclear localization signal.

The transactivation domain should be complementary to the DNA-binding domain, meaning that it should interact with the DNA-binding domain so as to activate transcription of a reporter gene comprising a binding site for the DNA-binding domain. Representative reporter genes enable genetic selection for prototrophy (e.g. LEU2, HIS3, or LYS2 reporters) or by screening with chromogenic substrates (lacZ reporter).

The fusion proteins can be expressed from a same vector or different vectors. The reporter gene can be expressed from a same vector as either fusion protein (or both proteins), or from a different vector. The bait, prey, and reporter genes are co-transfected into an assay cell, for example a microbial cell (e.g., a bacterial or yeast cell), an invertebrate cell (e.g., an insect cell), or a vertebrate cell (e.g., a mammalian cell, including a human cell). Cells that display activity of the encoded reporter are indicative of a binding interaction between the peptide and the candidate target molecule. The protein encoded by such a clone is identified using standard protocols known to one of skill in the art.

Additional methods for yeast two-hybrid analysis can be found in Brent & Finley (1997) *Annu Rev Genet* 31:663-704; Allen et al. (1995) *Trends Biochem Sci* 20:511-516; Lecrenier et al. (1998) *Bioessays* 20:1-5; Yang et al. (1995) *Nucleic Acids Res* 23:1152-1156; Bendixen et al. (1994) *Nucleic Acids Res* 22:1778-1779; Fuller et al. (1998) *Biotechniques* 25:85-88, 90-82; Cohen et al. (1998) *Proc Natl Acad Sci U S A* 95:14272-14277; Kolonin & Finley (1998) *Proc Natl Acad Sci U S A* 95:14266-14271; Vasavada et al. (1991) *Proc Natl Acad Sci U S A* 88:10686-10690; Rehrauer et al. (1996) *J Biol Chem* 271:23865-23873; and Fields & Song (1989) *Nature* 340:245-246.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the invention.

Example 1

X-Ray Guided Delivery of Fibrinogen-Conjugated Liposomes and Microspheres

Preparation of Radiolabeled Microspheres. Albumin microspheres (Martodam et al., 1979) were resuspended using 10 ml of sterile normal saline (0.9% NaCl). One-half milliliter of the reconstituted microsphere was added to a 1.5 ml conical polypropylene tube previously coated with Iodgen (Pierce of Rockford, Ill.). To this, 11.3 mCi (418 megabecquerel (MBq)) of $^{131}$I (DuPont Pharmaceuticals of Wilmington, Del.) was added in approximately 11 µl of saline and allowed to incubate at room temperature for 30 minutes. Following incubation, the microspheres were transferred to a 15 ml sterile centrifuge tube, diluted to 10 ml with normal saline and centrifuged at 1,500 g for seven minutes. The supernatant was removed and discarded. The microspheres were washed one additional time with 10 ml of normal saline and centrifuged. The microspheres were suspended in 2 ml of normal saline for injection. Final yield was 4.8 mCi (177.6 MBq) of radioiodinated microspheres in 2 ml saline. Radiochemical yield was 42.4%.

Preparation of Fibrinogen-Conjugated Liposomes. The lipophilic SH reactive reagent with a long spacing arm was synthesized from maleimide-PEG 2000-NSH ester (Prochem Chemicals of High Point, N.C.), dioleoylphosphatidylethanolanime (DOPE, available from AVANTI® Polar Lipids, Inc. of Alabaster, Ala.) and triethylamine in chloroform (1:1:1.5). Resulting maleimide-PEG 2000-DOPE was purified by flash column. Under stirring, to a solution of fibrinogen (2 mg/ml) in 0.01M HEPES 0.15 NaCl buffer pH 7.9, containing 10 mM EDTA and 0.08% NaN$_3$ was added in 5-fold excess of freshly prepared Traut's reagent (2-iminothiolane hydrochloride) in the same buffer. The reaction was allowed to proceed for 30 minutes at 0° C.

SH-fibrinogen was purified using a PD-10 desalting and buffer exchange column (Amersham Pharmacia Biotech of Piscataway, N.J.). PEG 2000-PE, cholesterol, Dipalmitoyl phosphocholine (AVANTI®) Polar Lipids, Inc. of Alabaster, Ala.), DiI (lipid fluorescent marker available from Molecular Probes of Eugene, Oreg.), and maleimide-PEG-2000-DOPE were dissolved in chloroform and mixed at a molar ratio of 10:43:43:2:2, respectively, in a round bottom flask. The organic solvent was removed by evaporation followed by desiccation under vacuum for 2 hours. Liposomes were prepared by hydrating the dried lipid film in PBS at a lipid concentration of 10 mM. The suspension was then sonicated 3×5 minutes, or until the solution appeared clear, to form unilamellar liposomes of 100 nM in diameter. To conjugate thiolated fibrinogen to maleimide containing liposomes, prepared vesicles and thiolated protein were mixed in 10 mm Hepes, 0.15M NaCl and EDTA pH 6.5. The final concentrations for proteins and liposomes were 0.25 g/L and 2.5 mM, respectively. The peptide/liposome mixture was incubated for 18 hours at room temperature. Vesicles were then separated from unconjugated peptide using a sepharose 4B-CL filtration column (Amersham Pharmacia Biotech of Piscataway, N.J.).

Liposomes were fluorescently labeled with DiI fluorescent marker (Molecular Probes, Inc. of Eugene, Oreg.) according to the manufacturer's instructions. Labeled liposomes were administered by tail vein injection to tumor bearing mice. Tumors were treated with 4 Gy either prior to administration or after administration of fibrinogen-liposome conjugates. Tumors were fixed and sectioned at 24 hours following irradiation. Fluorescence was imaged by ultraviolet microscopy (100×).

Image Analysis. Tumor bearing mice were imaged at one hour and 24 hours post-administration of radiolabeled proteins. Planar pinhole gamma camera imaging was performed on a single-head gamma camera (HELIX® model from General Electric Medical Systems of Milwaukee, Wis.) using a cone-shaped pinhole collimator with a 4-mm diameter Tungsten aperture. Pinhole collimation offers the advantage of improved photon detection efficiency (sensitivity) and spatial resolution when compared with conventional, parallel multihole collimators. Pinhole planar imaging with a small source-aperture separation can provide high-resolution images combined with large magnification. Each scan consisted of a 180-second acquisition (256×256 acquisition matrix) with a 10% energy window centered on 364 keV. The source-aperture separation was 6.0 cm.

Prior to imaging analysis in animals, a uniform $^{131}$I disk source was imaged in order to measure the angular dependence of the pinhole collimator—gamma camera system detection efficiency with distance from the center of the pinhole. Angular sensitivity, normalized to 1.0 at the center of the pinhole, was then used to scale the mouse data in order to correct image counts for this geometrical effect. A calibration source of known $^{131}$I activity was also scanned at a 6.0 cm source-aperture separation distance in order to measure system sensitivity along the center of the pinhole.

Peptide biodistribution data was assessed using two measures: (1) tumor-to-background ratio (T/B) of observed activity; and (2) tumor uptake activity in µCi. Both types of data were obtained using region-of-interest (ROI) analysis. For both measurements an 11×11 ROI was used to determine mean counts within the tumor ($\sigma_T$) and at five different locations within the mouse background ($\sigma_B$). These readings were scaled to account for geometric sensitivity and the ratio of tumor uptake to total animal uptake (R) was computed according to the relation, $$R = \frac{\sigma_T}{(\sigma_T + \sigma_B)}.$$

Activity uptake in the tumor was then approximated by the product of the amount of activity administered into the animal multiplied by the value obtained for R above. Tumor-background ratios were determined according to the general expression:

$$\left(\frac{T}{B}\right) = \frac{\sigma_T}{\sigma_B}.$$

Fibrinogen Coated Microsphere Localize to Irradiated Tumors.

Fibrinogen-coated microspheres were radiolabeled with $^{131}$I and administered by tail vein injection into tumor bearing mice, and tumors were irradiated with 6 Gy. The specificity of fibrinogen-coated albumin was determined by measuring the intensity of gamma detection within regions of interest (ROI) and well counts of tumor and other tissues. In animals receiving localized radiation at the tumor site, 90% of the measured radioactivity was localized to the tumor, and 10% of the radioactivity was diffusely distributed throughout the entire animal model. In untreated controls, 10% of radioactive counts were localized to the tumor (p<0.001).

During optimization studies, tumors were irradiated immediately before or immediately after tail vein injection. Both schedules were effective in achieving $^{131}$I-fibrinogen-coated microsphere binding. However, tumor irradiation subsequent to microsphere administration achieved increased targeting specificity when compared to tumors irradiated prior to microsphere administration. Microspheres lacking the fibrinogen ligand did not bind irradiated tumors.

To quantify a level of preferential binding of fibrinogen coated microspheres in irradiated tumors, data were normalized based on background levels of radiation. Fibrinogen-coated microspheres were 100-fold more abundant in irradiated tumors compared to non-tumor control tissues. By contrast, microspheres lacking the fibrinogen ligand were detected at similar levels in tumor and non-tumor control tissues.

To determine whether fibrinogen-conjugated microspheres bind irradiated non-tumor control tissues, the entire hind quarters of mice bearing hind limb tumors were irradiated, and radiolabeled fibrinogen-coated microspheres were administered immediately after irradiation. Well counts of all tissues were performed at 24 hours after irradiation. 90% of radioactive counts were detected in the tumor. By contrast, 2% of radioactive counts were detected in irradiated non-tumor control tissue, demonstrating selective targeting of fibrinogen-coated microspheres to irradiated tumors.

Fibrinogen-Liposome Conjugates Localize to Irradiated Tumors.

Fibrinogen-conjugated, fluorescently labeled liposomes were administered by tail vein into mice bearing tumors on both hind limbs. The right tumor was treated with radiation and the left tumor served as the untreated control. Untreated control tumors showed no fibrinogen-liposome conjugate binding whereas tumors irradiated immediately before or immediately after tail vein injection showed fibrinogen adhesion in blood vessels. The fluorescent marker was observed within the vascular lumen of tumor microvasculature.

Studies using radiolabeled fibrinogen-conjugated liposomes gave similar results. When liposomes were administered after tumor irradiation, 89% of fibrinogen-coated liposomes localized to tumors. When liposomes were administered immediately prior to tumor irradiation, 69% of liposomes showed tumor localization. By contrast, in untreated controls, a background level of 9% of fibrinogen-coated liposomes localized to the tumor.

Example 2

Clinical Trials of X-Ray-Guided Delivery Using a Peptide Ligand Ligand Preparation and Administration Biapcitide (ACUTECT® available from Diatide, Inc. of Londonderry, N.H.) is a synthetic peptide that binds to GP-IIb/IIIa receptors on activated platelets (Hawiger et al., 1989; Hawiger & Timmons, 1992). Biapcitide was labeled with $^{99m}$Tc in accordance with a protocol provided by Diatide Inc.

Reconstituted $^{99m}$Tc-labeled biapcitide was administered to patients at a dose of 100 mcg of biapcitide radiolabeled with 10 mCi of $^{99m}$Tc. Patients received $^{99m}$Tc-labeled biapcitide intravenously immediately prior to irradiation. Patients were then treated with 10 Gy or more. Patients underwent gamma camera imaging prior to irradiation and 24 hours following irradiation. Following planar image acquisition, those patients showing uptake in irradiated tumors underwent tomographic imaging using SPECT and repeat imaging at 24 hours. Patients showing no uptake on planer images during this 24-hour time frame had no further imaging. Each patient had an internal control, which consisted of a baseline scan immediately following administration of $^{99m}$Tc-labeled biapcitide.

Patients were treated with X-irradiation ranging from 4 to 18 MV photon using external beam linear accelerator at Vanderbilt University. Appropriate blocks, wedges and bolus to deliver adequate dose to the planned target volume was utilized. The site of irradiation, treatment intent and normal tissue considerations determined the radiation dosage and volume. When stereotactic radiosurgery was used, the dose was prescribed to the tumor periphery.

Image Analysis. Image acquisition consisted of both planar and single photon emission computed tomography (SPECT) studies. Planar studies were performed on a dual-head gamma camera (Millenium VG—Variable Geometry model available from General Electric Medical Systems of Milwaukee, Wis.) equipped with low energy high-resolution (LEUR) collimators. This type of collimator represents a compromise between sensitivity (photon counting efficiency) and image resolution. Planar nuclear medicine images were acquired with a 256×256 acquisition matrix (pixel size approximately 0.178 cm/pixel) for 10 minutes. In order to maximize collimator-gamma camera system sensitivity the source-to-detector surface distance was minimized to the extent that patient geometry allows. The spatial distribution of fibrinogen within the planar image was measured using region-of-interest (ROI) analysis. Two different size ROI's (5×5 pixel, and 15×15 pixel) was used in both the tumor and surrounding organs and tissues in the patient. The rationale for using ROIs with different dimensions is to be able to quantify image counts while at the same time isolating any possible influence of ROI size on the results. Tumor-to-background ratios were computed as the ratio of average counts in the tumor region divided by average counts in surrounding organs and tissues, each corrected for background. Background counts was determined based on ROI analysis of a separate planar acquisition performed in the absence of a radioactive source.

Three-dimensional nuclear medicine SPECT examinations were performed using the same dual-head gamma camera system. Each SPECT study comprised a 360 scan acquired with a step-and-shoot approach utilizing the following acquisition parameters: three increments between views, a 256×256×64 acquisition matrix, LEUR collimation and 60 seconds per view. Images were reconstructed using analytical filtered back-projection and statistical maximum likelihood techniques with photon attenuation correction and post-reconstruction deconvolution filtering for approximate detector response compensation. In this case, correction for background consisted of subtracting counts acquired in a single 60-second planar view from all views of the SPECT projection data prior to image reconstruction. SPECT tumor-to-background ratios were computed using quantitative ROI techniques identical to the planar studies.

Results. Administration of a $^{99m}$Tc-labeled biapticide, an RGD peptide mimetic, immediately prior to radiation resulted in tumor binding in 4 of 4 patients (Hallahan et al., 2001a). Two patients among this group had second neoplasms that were not treated with radiation, and binding of $^{99m}$Tc-labeled biapticide was not observed in the untreated tumor. Administration of the $^{99m}$Tc-labeled biapticide within one hour following radiation also failed to show localization of the targeting molecule to the tumor (Hallahan et al., 2001a).

Example 3

Response of Tumor Blood Vessels to Ionizing Radiation

To determine the response of tumor blood vessels to ionizing radiation, a tumor vascular window and Doppler sonography were used to measure the change in tumor blood vessels (Donnelly et al., 2001; Geng et al., 2001). Tumors implanted into the window model developed blood vessels within 1 week. Tumors were then treated with radiation and the response of blood vessels was imaged by use of light microscopy. Radiation doses in the range of 2-3 Gy increased the vascularity within tumors. In contrast, larger doses of radiation such as 6 Gy reduced tumor vascularity.

Established tumors were studied to determine whether there is a dose-dependent change in blood flow following irradiation. Tumors in the hind limb were grown to approximately 1 cm in diameter. Blood flow within tumors was measured by use of power Doppler (Donnelly et al., 2001). Tumors were treated with 3 Gy or 6 Gy ionizing radiation, and changes in tumor blood flow were measured using power Doppler sonography. A radiation dose of 3 Gy achieved an increase in tumor blood flow. In contrast, radiation doses of 6 Gy or higher markedly reduced tumor blood flow.

Example 4

Preparation of a Recombinant Peptide Library in Phage

A population of DNA fragments encoding recombinant peptide sequences was cloned into the T7 SELECT™ vector (Novagen of Madison, Wis.). Cloning at the EcoR I restriction enzyme recognition site places the recombinant peptide in-frame with the 10B protein such that the peptide is displayed on the capsid protein. The resulting reading frame requires an AAT initial codon followed by a TCX codon.

The molar ratio between insert and vector was 1:1. Size-fractionated cDNA inserts were prepared by gel filtration on sepharose 4B and ranged from 27 base pairs to 33 base pairs. cDNAs were ligated by use of the DNA ligation kit (Novagen of Madison, Wis.). Recombinant T7 DNA was packaged according to the manufacturer's instructions and amplified prior to biopanning in animal tumor models. The diversity of the library was $10^7$.

Example 5

In vivo Panning for Peptide Ligands to Radiation-Induced Molecules

GL261 murine glioma cells and Lewis lung carcinoma cells were implanted into the hind limb of C57BL6 mice (Hallahan et al., 1995b; Hallahan et al., 1998; Hallahan & Virudachalam, 1999).

To determine the optimal time at which peptides bind within tumors, phage were administered at 1 hour before, at 1 hour after, and at 4 hours after irradiation of both LLC and GL261 tumors. Phage were recovered from tumors when administered 4 hours after irradiation. Phage administered 1 hour before or 1 hour after irradiation were not recovered from tumors. These data indicate that the optimal time of administration is beyond 1 hour after irradiation.

For in vivo panning, tumors were irradiated with 3 Gy and approximately $10^{10}$ phage (prepared as described in Example 4) were administered by tail vein injection into each of the tumor bearing mice at 4 hours following irradiation. Tumors were recovered at one hour following injection and amplified in BL21 bacteria. Amplified phage were pooled and re-administered to a tumor-bearing mouse following tumor irradiation. The phage pool was sequentially administered to a total of 6 animals. As a control, wild type phage lacking synthetic peptide inserts were identically administered to a second experimental group of animals.

To determine the titer of phage binding in a tumor or in normal tissue, recovered phage were amplified in BL21 bacteria. Bacteria were plated and the number of plaques present were counted. To determine the total phage output per organ, the number of plaque forming units (PFU) on each plate was divided by the volume of phage plated and the weight of each organ. Normal variation was observed as a 2-fold difference in PFU.

In the present study, background binding within tumor blood vessels was approximately $10^4$ phage. Phage that bound to the vasculature within irradiated tumors show enrichment in the tumor relative to other organs and enrichment in the irradiated tumor relative to the control phage without DNA insert. Phage that home to irradiated tumors showed a background level of binding in control organs that was lower than control phage without DNA insert.

Following 6 rounds of in vivo panning, fifty recombinant phage peptides that bound within irradiated tumors were randomly selected for further analysis. The nucleic acid sequence encoding recombinant phage was amplified by PCR using primers set forth as SEQ ID NOs:14-15 (available from Novagen of Madison, Wis.). An individual phage suspension was used as template. Amplified peptides were sequenced using an ABI PRISM 377 sequencer (Applied Biosystems of Foster City, Calif.). The sequences of the encoded peptides are listed in Table 1. Several conserved subsequences were deduced from the recovered peptides and are presented in Table 2.

Peptide sequences recovered from both tumor types include NHVGGSSV (SEQ ID NO:1), NSLRGDGSSV (SEQ ID NO:2), and NSVGSRV (SEQ ID NO:4). Of the peptide sequences recovered from 6 irradiated tumors, 56% had the subsequence GSSV (SEQ ID NO:5), 18% had the sequence RGDGSSV (SEQ ID NO:6), and 4% had the sequence GSRV (SEQ ID NO:7). Approximately 22-40 of $10^6$ injected phage were recovered from irradiated tumors having a peptide insert comprising the subsequence GSSV (SEQ ID NO:5). By contrast, no phage were from irradiated tumors following administration of $10^6$ wild type phage.

TABLE 1

Peptides Identified by In Vivo Panning of LLC and GL261 Tumors

| Peptide Sequence | Number of Phage Recovered from LLC tumors (Frequency) | Number of Phage Recovered from GL261 tumors (Frequency) |
|---|---|---|
| NHVGGSSV (SEQ ID NO:1) | 7 (28%) | 12 (48%) |
| NSLRGDGSSV (SEQ ID NO:2) | 7 (28%) | 2 (8%) |
| NSVRGSGSGV (SEQ ID NO:3) | 7 (28%) | 0 |
| NSVGSRV (SEQ ID NO:4) | 1 (4%) | 3 (12%) |
| Unique Sequences | 3 (12%) | 8 (32%) |

TABLE 2

Conserved Motifs within Peptides Identified by In Vivo Panning

| Conserved Sequence | Frequency of Recovery |
|---|---|
| GSSV (SEQ ID NO:13) | 56% |
| GSXV (SEQ ID NO:8) | 78% |
| NSXRGXGS (SEQ ID NO:9) | 32% |
| NSV (SEQ ID NO:10) | 22% |
| NSXR (SEQ ID NO:11) | 32% |
| NXVG (SEQ ID NO:12) | 46% |

Example 6

Peptide Targeting in Additional Tumors

The binding properties of phage encoding NHVGGSSV (SEQ ID NO:1), NSLRGDGSSV (SEQ ID NO:2), NSVRGSGSGV (SEQ ID NO:3), and NSVGSRV (SEQ ID NO:4) were additionally characterized in a B16F0 melanoma model. Peptides set forth as SEQ ID NOs:1 and 2 bound within the melanoma, lung carcinoma, and glioma tumor models. SEQ ID NO:3 bound within glioma and melanoma, and SEQ ID NO:4 bound within lung carcinoma and glioma.

Example 7

Characterization of Peptide Binding to Irradiated Tumors

To determine where recombinant peptides bind in tumor blood vessels, the biodistribution of biotinylated peptides was assessed. Tumors were treated with 3 Gy and biotinylated peptides were administered by tail vein at 4 hours following irradiation. Tumors were recovered 30 minutes following administration of biotinylated peptides. Tumors were snap frozen and sectioned on a cryostat. Frozen sections were then incubated with Avidin-FITC (fluorescein isothiocyante) and imaged by fluorescent microscopy. Recombinant peptides (for example, those set forth in Table 1) were observed to bind the vascular endothelium within tumor blood vessels.

The anti-$\alpha_{2b}\beta_3$ monoclonal antibody was administered by tail vein to determine whether this receptor is required for recombinant phage binding in irradiated tumors. Phage encoding SLRGDGSSV (SEQ ID NO:5) on the capsid protein were injected immediately after blocking antibody or control antibody. Phage were recovered from the tumor and controls organs and quantified by plaque formation. Radiation induced a 4-fold increase in phage binding in tumor. Blocking antibody eliminated induction of phage binding, while control antibody to P-selectin (on activated platelets) did not reduce phage binding. Thus, the tumor binding activity of targeting peptide SLRGDGSSV (SEQ ID NO:5) is dependent on its interaction with the $\alpha_{2b}\beta_3$ receptor.

Example 8

In vivo Panning for Antibody Ligands to Radiation-Induced Molecules

A phage library comprising diverse single chain antibodies was prepared in M13 phage. The phage library was exposed to the radiation-induced neoantigens P-selectin (also called CD62P; GenBank Accession No. P98109) and/or platelet membrane glycoprotein IIB (also called CD41; GenBank Accession No. P08514) immobilized on glass slides. Phage were selected based on antigen binding, and selected phage were pooled as a biased library. For representative in vitro panning methods, see Fowlkes et al. (1992) *Biotechniques* 13:422-428; Haaparanta & Huse (1995) *Mol Divers* 1:39-52; Jung & Pluckthun (1997) *Protein Eng* 10:959-966; Peter et al. (2000) *Circulation* 101:1158-1164; and Holzem et al. (2001) *J Gen Virol* 82:9-15; Chiu et al. (2000) *J Agric Food Chem* 48:2614-2624.

Phage identified by in vitro panning were tested on Western immunoblots to confirm binding to the P-selection and platelet membrane glycoprotein IIB neoantigens. Phage that specifically bound P-selectin and platelet membrane glycoprotein IIB were subsequently used for in vivo panning to irradiated tumors as described in Example 5. Wild type phage were used as internal controls. Antibodies having substantial affinity for irradiated tumors were identified by observing an increased number of phage in the irradiated tumor when compared to a number of phage in a control organ (e.g., liver and lung). Phage antibodies with the greatest affinity for tumors were identified using the formula: number of phage in irradiated tumor/number of phage in each organ.

Eight antibodies that bound P-selectin and fifteen antibodies that bound platelet membrane glycoprotein IIB were recovered following in vivo panning to irradiated tumors. Representative targeting antibodies identified by this method include the single chain antibodies set forth as SEQ ID NOs: 18 and 20 (encoded by SEQ ID NOs:17 and 19, respectively), that recognize the radiation-induced neoantigens P-selectin and platelet membrane glycoprotein IIB, respectively.

REFERENCES

The references listed below as well as all references cited in the specification are incorporated herein by reference to the extent that they supplement, explain, provide a background for or teach methodology, techniques and/or compositions employed herein.

Aboud-Pirak E, Lesur B, Rao K S, Baurain R, Trouet A & Schneider Y J (1989) Cytotoxic activity of daunorubicin or vindesin conjugated to a monoclonal antibody on cultured MCF-7 breast carcinoma cells. Biochem Pharmacol 38:641-648.

Albini A, Marchisone C, Del Grosso F, Benelli R, Masiello L, Tacchetti C, Bono M, Ferrantini M, Rozera C, Truini M, Belardelli F, Santi L & Noonan DM (2000) Inhibition of angiogenesis and vascular tumor growth by interferon-producing cells: A gene therapy approach. Am J Pathol 156:1381-1393.

Allen J B, Walberg M W, Edwards M C & Elledge S J (1995) Finding prospective partners in the library: the two-hybrid system and phage display find a match. Trends Biochem Sci 20:511-516.

Altschul S F, Gish W, Miller W, Myers E W & Lipman D J (1990) Basic local alignment search tool. J Mol Biol 215: 403-410.

Amemiya Y, Satow Y, Matsushita T, Chikawa J, Wakabayashi K, Miyahara J & Mandelkow E (1988) Storage Phosphor Detector.

Andersson L, Blomberg L, Flegel M, Lepsa L, Nilsson B & Verlander M (2000) Large-scale synthesis of peptides. Biopolymers 55:227-250.

Arap W, Pasqualini R & Ruoslahti E (1998) Cancer treatment by targeted drug delivery to tumor vasculature in a mouse model. Science 279:377-380.

Ausubel F, ed (1995) Short Protocols in Molecular Biology, 3rd ed. Wiley, New York.

Baillie C T, Winslet M C & Bradley N J (1995) Tumour vasculature—a potential therapeutic target. Br J Cancer 72:257-267.

Barton G J (1998) Protein sequence alignment techniques. Acta Crystallogr D Biol Crystallogr 54:1139-1146.

Batzer M A, Carlton J E & Deininger P L (1991) Enhanced evolutionary PCR using oligonucleotides with inosine at the 3'-terminus. Nucleic Acids Res 19:5081.

Bauminger S & Wilchek M (1980) The use of carbodiimides in the preparation of immunizing conjugates. Methods Enzymol 70:151-159.

Becerril B, Poul M A & Marks J D (1999) Toward selection of internalizing antibodies from phage libraries. Biochem Biophys Res Commun 255:386-393.

Bendixen C, Gangloff S & Rothstein R (1994) A yeast mating-selection scheme for detection of protein-protein interactions. Nucleic Acids Res 22:1778-1779.

Bodanszky M (1993) Principles of Peptide Synthesis, 2nd rev. ed. Springer-Verlag, Berlin/New York.

Boerman O C, Oyen W J & Corstens F H (2000) Radiolabeled receptor-binding peptides: a new class of radiopharmaceuticals. Semin Nucl Med 30:195-208.

Brenner S & Lerner R A (1992) Encoded combinatorial chemistry. Proc Natl Acad Sci U S A 89:5381-5383.

Brent R & Finley R L, Jr. (1997) Understanding gene and allele function with two-hybrid methods. Annu Rev Genet 31:663-704.

Buchsbaum D, Khazaeli M B, Liu T, Bright S, Richardson K, Jones M & Meredith R (1995) Fractionated radioimmunotherapy of human colon carcinoma xenografts with $^{131}$I-labeled monoclonal antibody CC49. Cancer Res 55:5881s-5887s.

Burg M A, Pasqualini R, Arap W, Ruoslahti E & Stallcup W B (1999) NG2 proteoglycan-binding peptides target tumor neovasculature. Cancer Res 59:2869-2874.

Carninci P, Kvam C, Kitamura A, Ohsumi T, Okazaki Y, Itoh M, Kamiya M, Shibata K, Sasaki N, Izawa M, Muramatsu M, Hayashizaki Y & Schneider C (1996) High-efficiency full-length cDNA cloning by biotinylated CAP trapper. Genomics 37:327-336.

Carpizo D & Iruela-Arispe M L (2000) Endogenous regulators of angiogenesis—emphasis on proteins with thrombospondin—type I motifs. Cancer Metastasis Rev 19:159-165.

Chattopadhyay S, Das M K, Vanaja R & Ramamoorthy N (2001) Purification and stabilization of 99mTc-d,l-HMPAO: role of organic extractants. Nucl Med Biol 28:741-744.

Cheng P W (1996) Receptor ligand-facilitated gene transfer: enhancement of liposome-mediated gene transfer and expression by transferrin. Hum Gene Ther 7:275-282.

Cheng S, Craig W S, Mullen D, Tschopp J F, Dixon D & Pierschbacher M D (1994) Design and synthesis of novel cyclic RGD-containing peptides as highly potent and selective integrin alpha lib beta 3 antagonists. J Med Chem 37:1-8.

Chiu Y W, Chen R, Li Q X & Karu A E (2000) Derivation and properties of recombinant Fab antibodies to coplanar polychlorinated biphenyls. J Agric Food Chem 48:2614-2624.

Clapp C, Martial J A, Guzman R C, Rentier-Delure F & Weiner R I (1993) The 16-kilodalton N-terminal fragment of human prolactin is a potent inhibitor of angiogenesis. Endocrinology 133:1292-1299.

Coatney R W (2001) Ultrasound imaging: principles and applications in rodent research. liar J 42:233-247.

Cohen B A, Colas P & Brent R (1998) An artificial cell-cycle inhibitor isolated from a combinatorial library. Proc Natl Acad Sci U S A 95:14272-14277.

Corringer P J, Weng J H, Ducos B, Durieux C, Boudeau P, Bohme A & Roques B P (1993) CCK-B agonist or antagonist activities of structurally hindered and peptidase-resistant Boc-CCK4 derivatives. J Med Chem 36:166-172.

Dameron K M, Volpert O V, Tainsky M A & Bouck N (1994) Control of angiogenesis in fibroblasts by p53 regulation of thrombospondin-1. Science 265:1582-1584.

Deutscher M P (1990) Guide to Protein Purification, Academic Press, San Diego.

Dewanjee M K, Ghafouripour A K, Kapadvanjwala M, Dewanjee S, Serafini A N, Lopez D M & Sfakianakis G N (1994) Noninvasive imaging of c-myc oncogene messenger RNA with indium-111-antisense probes in a mammary tumor-bearing mouse model. J Nucl Med 35:1054-1063.

Dias S, Thomas H & Balkwill F (1998) Multiple molecular and cellular changes associated with tumour stasis and regression during IL-12 therapy of a murine breast cancer model. Int J Cancer 75:151-157.

Dillman R O, Johnson D E, Ogden J & Beidler D (1989) Significance of antigen, drug, and tumor cell targets in the preclinical evaluation of doxorubicin, daunorubicin, methotrexate, and mitomycin-C monoclonal antibody immunoconjugates. Mol Biother 1:250-255.

Donnelly E F, Geng L, Wojcicki W E, Fleischer A C & Hallahan D E (2001) Quantified power Doppler US of tumor blood flow correlates with microscopic quantification of tumor blood vessels. Radiology 219:166-170.

Eijan A M, Davel L, Oisgold-Daga S & de Lustig E S (1991) Modulation of tumor-induced angiogenesis by proteins of extracellular matrix. Mol Biother 3:38-40.

Ellerby H M, Arap W, Ellerby L M, Kain R, Andrusiak R, Rio G D, Krajewski S, Lombardo C R, Rao R, Ruoslahti E, Bredesen D E & Pasqualini R (1999) Anti-cancer activity of targeted pro-apoptotic peptides. Nat Med 5:1032-1038.

European Patent No. 0 439 095

Fields G B & Noble R L (1990) Solid phase peptide synthesis utilizing 9-fluorenylmethoxycarbonyl amino acids. Int J Pept Protein Res 35:161-214.

Fjalling M, Andersson P, Forssell-Aronsson E, Gretarsdottir J, Johansson V, Tisell L E, Wangberg B, Nilsson O, Berg G, Michanek A, Lindstedt G & Ahiman H (1996) Systemic radionuclide therapy using indium-111-DTPA-D-Phe1-octreotide in midgut carcinoid syndrome. J Nucl Med 37:1519-1521.

Fields S & Song O (1989) A novel genetic system to detect protein-protein interactions. Nature 340:245-246.

Fitzpatrick J J & Garnett M C (1995) Design, synthesis and in vitro testing of methotrexate carrier conjugates linked via oligopeptide spacers. Anticancer Drug Des 10:1-9.

Fowlkes D M, Adams M D, Fowler V A & Kay B K (1992) Multipurpose vectors for peptide expression on the M13 viral surface. Biotechniques 13:422-428.

Fraser S E (1996) Iontophoretic dye labeling of embryonic cells. Methods Cell Biol 51:147-160.

Fuller K J, Morse M A, White J H, Dowell S J & Sims M J (1998) Development of a yeast trihybrid screen using stable yeast strains and regulated protein expression. Biotechniques 25:85-88, 90-82.

Garbay-Jaureguiberry C, Ficheux D & Roques B P (1992) Solid phase synthesis of peptides containing the non-hydrolysable analog of (O)phosphotyrosine, p(CH2PO3H2) Phe. Application to the synthesis of 344-357 sequences of the beta 2 adrenergic receptor. Int J Pept Protein Res 39:523-527.

Geng L, Donnelly E, McMahon G, Lin P C, Sierra-Rivera E, Oshinka H & Hallahan D E (2001) Inhibition of vascular endothelial growth factor receptor signaling leads to reversal of tumor resistance to radiotherapy. Cancer Res 61:2413-2419.

Glover D M & Hames B D (1995) DNA Cloning: A Practical Approach, 2nd ed. IRL Press at Oxford University Press, Oxford/New York.

Goldman C K, Rogers B E, Douglas J T, Sosnowski B A, Ying W, Siegal G P, Baird A, Campain J A & Curiel D T (1997) Targeted gene delivery to Kaposi's sarcoma cells via the fibroblast growth factor receptor. Cancer Res 57:1447-1451.

Haaparanta T & Huse W D (1995) A combinatorial method for constructing libraries of long peptides displayed by filamentous phage. Mol Divers 1:39-52.

Hallahan D, Kuchibhotla J & Wyble C (1996) Cell adhesion molecules mediate radiation-induced leukocyte adhesion to the vascular endothelium. Cancer Res 56:5150-5155.

Hallahan D, Clark E T, Kuchibhotla J, Gewertz B L & Collins T (1995a) E-selectin gene induction by ionizing radiation is independent of cytokine induction. Biochem Biophys Res Commun 217:784-795.

Hallahan D E & Virudachalam S (1999) Accumulation of P-selectin in the lumen of irradiated blood vessels. Radiat Res 152:6-13.

Hallahan D E, Staba-Hogan M J, Virudachalam S & Kolchinsky A (1998) X-ray-induced P-selectin localization to the lumen of tumor blood vessels. Cancer Res 58:5216-5220.

Hallahan D E, Geng L, Cmelak A J, Chakravarthy A B, Martin W, Scarfone C & Gonzalez A (2001a) Targeting drug delivery to radiation-induced neoantigens in tumor microvasculature. J Control Release 74:183-191.

Hallahan D E, Qu S, Geng L, Cmelak A, Chakravarthy A, Martin W, Scarfone C & Giorgio T (2001b) Radiation-Mediated Control of Drug Delivery. Am J Clin Oncol: in press.

Hallahan D E, Mauceri H J, Seung L P, Dunphy E J, Wayne J D, Hanna N N, Toledano A, Hellman S, Kufe D W & Weichselbaum R R (1995b) Spatial and temporal control of gene therapy using ionizing radiation. Nat Med 1:786-791.

Hartmann F, Horak E M, Garmestani K, Wu C, Brechbiel M W, Kozak R W, Tso J, Kosteiny S A, Gansow O A, Nelson D L & et al. (1994) Radioimmunotherapy of nude mice bearing a human interleukin 2 receptor alpha-expressing lymphoma utilizing the alpha-emitting radionuclide-conjugated monoclonal antibody 212Bi-anti-Tac. Cancer Res 54:4362-4370.

Hawiger J & Timmons S (1992) Binding of fibrinogen and von Willebrand factor to platelet glycoprotein IIb-IIa complex. Methods Enzymol 215:228-243.

Hawiger J, Kloczewiak M, Bednarek M A & Timmons S (1989) Platelet receptor recognition domains on the alpha chain of human fibrinogen: structure-function analysis. Biochemistry 28:2909-2914.

Healy J M, Murayama O, Maeda T, Yoshino K, Sekiguchi K & Kikuchi M (1995) Peptide ligands for integrin alpha v beta 3 selected from random phage display libraries. Biochemistry 34:3948-3955.

Henikoff J G, Pietrokovski S, McCallum C M & Henikoff S (2000) Blocks-based methods for detecting protein homology. Electrophoresis 21:1700-1706.

Henikoff S & Henikoff J G (1992) Amino acid substitution matrices from protein blocks. Proc Natl Acad Sci U S A 89:10915-10919.

Henn T F, Garnett M C, Chhabra S R, Bycroft B W & Baldwin R W (1993) Synthesis of 2'-deoxyuridine and 5-fluoro-2'-deoxyuridine derivatives and evaluation in antibody targeting studies. J Med Chem 36:1570-1579.

Heredia M, Santacana M & Valverde F (1991) A method using DiI to study the connectivity of cortical transplants. J Neurosci Methods 36:17-25.

Hnatowich D J, Mardirossian G, Fogarasi M, Sano T, Smith C L, Cantor C R, Rusckowski M & Winnard P, Jr. (1996) Comparative properties of a technetium-99m-labeled single-stranded natural DNA and a phosphorothioate derivative in vitro and in mice. J Pharmacol Exp Ther 276:326-334.

Holzem A, Nahring J M & Fischer R (2001) Rapid identification of a tobacco mosaic virus epitope by using a coat protein gene-fragment-pVIII fusion library. J Gen Virol 82:9-15.

Huang C C, Novak W R, Babbitt P C, Jewett A I, Ferrin T E & Klein T E (2000) Integrated tools for structural and sequence alignment and analysis. Pac Symp Biocomput: 230-241.

Ingber D, Fujita T, Kishimoto S, Sudo K, Kanamaru T, Brem H & Folkman J (1990) Synthetic analogues of fumagillin that inhibit angiogenesis and suppress tumour growth. Nature 348:555-557.

Ishikawa E (1999) Ultrasensitive and rapid enzyme immunoassay. Elsevier, Amsterdam/New York.

Ito T, Qiu H, Collins J A, Brill A B, Johnson D K & Griffin T W (1991) Preclinical assessments of 90Y-labeled C110 anti-carcinoembryonic antigen immunotoxin: a therapeutic immunoconjugate for human colon cancer. Cancer Res 51:255-260.

Julien M, Kajiji S, Kaback R H & Gros P (2000) Simple purification of highly active biotinylated P-glycoprotein: enantiomer-specific modulation of drug-stimulated ATPase activity. Biochemistry 39:75-85.

Jung S & Pluckthun A (1997) Improving in vivo folding and stability of a single-chain Fv antibody fragment by loop grafting. Protein Eng 10:959-966.

Karlin S & Altschul SF (1993) Applications and statistics for multiple high-scoring segments in molecular sequences. Proc Natl Acad Sci U S A 90:5873-5877.

Kirk C J & Mule J J (2000) Gene-modified dendritic cells for use in tumor vaccines. Hum Gene Ther 11:797-806.

Kirpotin D, Park J W, Hong K, Zalipsky S, Li W L, Carter P, Benz C C & Papahadjopoulos D (1997) Sterically stabilized anti-HER2 immunoliposomes: design and targeting to human breast cancer cells in vitro. Biochemistry 36:66-75.

Koivunen E, Gay D A & Ruoslahti E (1993) Selection of peptides binding to the alpha 5 beta 1 integrin from phage display library. J Biol Chem 268:20205-20210.

Koivunen E, Wang B & Ruoslahti E (1994) Isolation of a highly specific ligand for the alpha 5 beta 1 integrin from a phage display library. J Cell Biol 124:373-380.

Kolonin M G & Finley R L, Jr. (1998) Targeting cyclin-dependent kinases in Drosophila with peptide aptamers. Proc Natl Acad Sci U S A 95:14266-14271.

Kosfeld M D & Frazier W A (1993) Identification of a new cell adhesion motif in two homologous peptides from the COOH-terminal cell binding domain of human thrombospondin. J Biol Chem 268:8808-8814.

Krauer K G, McKenzie I F & Pietersz G A (1992) Antitumor effect of 2'-deoxy-5-fluorouridine conjugates against a murine thymoma and colon carcinoma xenografts. Cancer Res 52:132-137.

Krenning E P & de Jong M (2000) Therapeutic use of radiolabelled peptides. Ann Oncol 11:267-271.

Kwekkeboom D, Krenning E P & de Jong M (2000) Peptide receptor imaging and therapy. J Nucl Med 41:1704-1713.

Kyte J & Doolittle R F (1982) A simple method for displaying the hydropathic character of a protein. J Mol Biol 157:105-132.

Law B (1996) Immunoassay: A Practical Guide. Taylor & Francis, London/Bristol, Pa.

Lau A, Berube G & Ford C H (1995) Conjugation of doxorubicin to monoclonal anti-carcinoembryonic antigen antibody via novel thiol-directed cross-linking reagents. Bioorg Med Chem 3:1299-1304.

Lecrenier N, Foury F & Goffeau A (1998) Two-hybrid systematic screening of the yeast proteome. Bioessays 20:1-5.

Lees W (2001) Ultrasound imaging in three and four dimensions. Semin Ultrasound CT MR 22:85-105.

Leibel S A & Phillips T L (1998) Textbook of Radiation Oncology. Saunders, Philadelphia.

Licha K, Riefke B, Ntziachristos V, Becker A, Chance B & Semmler W (2000) Hydrophilic cyanine dyes as contrast agents for near-infrared tumor imaging: synthesis, photophysical properties and spectroscopic in vivo characterization. Photochem Photobiol 72:392-398.

Lu Z, Murray K S, Van Cleave V, LaVallie E R, Stahl M L & McCoy J M (1995) Expression of thioredoxin random peptide libraries on the *Escherichia coli* cell surface as functional fusions to flagellin: a system designed for exploring protein-protein interactions. Biotechnology (N Y) 13:366-372.

Mackensen A, Lindemann A & Mertelsmann R (1997) Immunostimulatory cytokines in somatic cells and gene therapy of cancer. Cytokine Growth Factor Rev 8:119-128.

Maione T E, Gray G S, Petro J, Hunt A J, Donner A L, Bauer S I, Carson H F & Sharpe R J (1990) Inhibition of angiogenesis by recombinant human platelet factor-4 and related peptides. Science 247:77-79.

Manome Y, Abe M, Hagen M F, Fine H A & Kufe D W (1994) Enhancer sequences of the DF3 gene regulate expression of the herpes simplex virus thymidine kinase gene and confer sensitivity of human breast cancer cells to ganciclovir. Cancer Res 54:5408-5413.

Manson M M (1992) Immunochemical Protocols. Humana Press, Totowa, N.J.

Martodam R R, Twumasi D Y, Liener I E, Powers J C, Nishino N & Krejcarek G (1979) Albumin microspheres as carrier of an inhibitor of leukocyte elastase: potential therapeutic agent for emphysema. Proc Natl Acad Sci U S A 76:2128-2132.

McOmie J F W. (1973) Protective Groups in Organic Chemistry, Plenum Press, London, New York.

Merrifield R B (1969) Solid-phase peptide synthesis. Adv Enzymol Relat Areas Mol Biol 32:221-296.

Nabel G (1997) Vectors for Gene Therapy. In: Current Protocols in Human Genetics, John Wiley & Sons, New York.

Narvaiza I, Mazzolini G, Barajas M, Duarte M, Zaratiegui M, Qian C, Melero I & Prieto J (2000) Intratumoral coinjection of two adenoviruses, one encoding the chemokine IFN-gamma-inducible protein-10 and another encoding IL-12, results in marked antitumoral synergy. J Immunol 164:3112-3122.

Needleman S B & Wunsch C D (1970) A general method applicable to the search for similarities in the amino acid sequence of two proteins. J Mol Biol 48:443-453.

Neri D, Carnemolla B, Nissim A, Leprini A, Querze G, Balza E, Pini A, Tarli L, Halin C, Neri P, Zardi L & Winter G (1997) Targeting by affinity-matured recombinant antibody fragments of an angiogenesis associated fibronectin isoform. Nat Biotechnol 15:1271-1275.

Nomura T & Hasegawa H (2000) Chemokines and anti-cancer immunotherapy: anti-tumor effect of EBI1-ligand chemokine (ELC) and secondary lymphoid tissue chemokine (SLC). Anticancer Res 20:4073-4080.

O'Byrne K J, Dalgleish A G, Browning M J, Steward W P & Harris A L (2000) The relationship between angiogenesis and the immune response in carcinogenesis and the progression of malignant disease. Eur J Cancer 36:151-169.

O'Reilly M S, Holmgren L, Shing Y, Chen C, Rosenthal R A, Moses M, Lane W S, Cao Y, Sage E H & Folkman J (1994) Angiostatin: a novel angiogenesis inhibitor that mediates the suppression of metastases by a Lewis lung carcinoma. Cell 79:315-328.

O'Reilly M S, Boehm T, Shing Y, Fukai N, Vasios G, Lane W S, Flynn E, Birkhead J R, Olsen B R & Folkman J (1997) Endostatin: an endogenous inhibitor of angiogenesis and tumor growth. Cell 88:277-285.

Ohtsuka E, Matsuki S, Ikehara M, Takahashi Y & Matsubara K (1985) An alternative approach to deoxyoligonucleotides as hybridization probes by insertion of deoxyinosine at ambiguous codon positions. J Biol Chem 260:2605-2608.

Park J W, Hong K, Kirpotin D B, Papahadjopoulos D & Benz C C (1997) Immunoliposomes for cancer treatment. Adv Pharmacol 40:399-435.

Pasqualini R & Ruoslahti E (1996) Organ targeting in vivo using phage display peptide libraries. Nature 380:364-366.

Pasqualini R, Koivunen E & Ruoslahti E (1997) Alpha v integrins as receptors for tumor targeting by circulating ligands. Nat Biotechnol 15:542-546.

Pavone V, Di Blasio B, Lombardi A, Maglio O, Isernia C, Pedone C, Benedetti E, Altmann E & Mutter M (1993) Non coded C alpha, alpha-disubstituted amino acids. X-ray diffraction analysis of a dipeptide containing (S)-alpha-methylserine. Int J Pept Protein Res 41:15-20.

Pearson W R & Lipman D J (1988) Improved tools for biological sequence comparison. Proc Natl Acad Sci U S A 85:2444-2448.

Peter K, Graeber J, Kipriyanov S, Zewe-Welschof M, Runge M S, Kubler W, Little M & Bode C (2000) Construction and functional evaluation of a single-chain antibody fusion protein with fibrin targeting and thrombin inhibition after activation by factor Xa. Circulation 101:1158-1164.

Pierschbacher M D & Ruoslahti E (1987) Influence of stereochemistry of the sequence Arg-Gly-Asp-Xaa on binding specificity in cell adhesion. J Biol Chem 262:17294-17298.

Pomper M G & Port J D (2000) New techniques in MR imaging of brain tumors. Magn Reson Imaging Clin N Am 8:691-713.

Ragnarson B, Bengtsson L & Haegerstrand A (1992) Labeling with fluorescent carbocyanine dyes of cultured endothelial and smooth muscle cells by growth in dye-containing medium. Histochemistry 97:329-333.

Rehrauer W M, Lavery P E, Palmer E L, Singh R N & Kowalczykowski S C (1996) Interaction of *Escherichia coli* RecA protein with LexA repressor. I. LexA repressor cleavage is competitive with binding of a secondary DNA molecule. J Biol Chem 271:23865-23873.

Rossolini G M, Cresti S, Ingianni A, Cattani P, Riccio M L & Satta G (1994) Use of deoxyinosine-containing primers vs degenerate primers for polymerase chain reaction based on ambiguous sequence information. Mol Cell Probes 8:91-98.

Rovaris M, Comi G & Filippi M (2001) The role of non-conventional MR techniques to study multiple sclerosis patients. J Neurol Sci 186 Suppl 1:S3-9.

Rowland A J, Pietersz G A & McKenzie I F (1993) Preclinical investigation of the antitumour effects of anti-CD19-idarubicin immunoconjugates. Cancer Immunol Immunother 37:195-202.

Sagiuchi T, Ishii K, Asano Y, Aoki Y, Woodhams R, Yanaihara H, Kan S & Hayakawa K (2001) Transient seizure activity demonstrated by Tc-99m HMPAO SPECT and diffusion-weighted MR imaging. Ann Nucl Med 15:267-270.

Sakamoto N, Iwahana M, Tanaka N G & Osada Y (1991) Inhibition of angiogenesis and tumor growth by a synthetic laminin peptide, CDPGYIGSR-NH2. Cancer Res 51:903-906.

Saltzman W M & Fung L K (1997) Polymeric implants for cancer chemotherapy. Adv Drug Deliv Rev 26:209-230.

Sambrook J & Russell D W (2001) Molecular Cloning: a Laboratory Manual, 3rd ed. Cold Spring Harbor Laboratory Press, Cold Spring Harbor, N.Y.

Saqi M A, Wild D L & Hartshorn M J (1999) Protein analyst—a distributed object environment for protein sequence and structure analysis. Bioinformatics 15:521-522.

Schechter B, Arnon R, Wilchek M, Schlessinger J, Hurwitz E, Aboud-Pirak E & Sela M (1991) Indirect immunotargeting of cis-Pt to human epidermoid carcinoma KB using the avidin-biotin system. Int J Cancer 48:167-172.

Schneider C H & Eberle A N (1993) Peptides, 1992: Proceedings of the Twenty-Second European Peptide Symposium, Sep. 13-19, 1992, Interlaken, Switzerland, Escom, Leiden.

Schröder E & Lübke K (1965) The Peptides, Academic Press, New York. Schwendener R (1992) Liposomes and Immunoliposomes as Carriers for Cytostatic Drugs, Magnetic Resonance Contrast Agents, and Fluorescent Chelates. Chimia 46:69-77.

Shawler D L, Johnson D E, Sweet M D, Myers L J, Tudor S D, Beidler D E, Koziol J A & Dillman R O (1988) Preclinical trials using an immunoconjugate of T101 and methotrexate in an athymic mouse/human T-cell tumor model. J Biol Response Mod 7:608-618.

Shen T, Weissleder R, Papisov M, Bogdanov A, Jr. & Brady T J (1993) Monocrystalline iron oxide nanocompounds (MION): physicochemical properties. Magn Reson Med 29:599-604.

Shih L B, Goldenberg D M, Xuan H, Lu H W, Mattes M J & Hall T C (1994) Internalization of an intact doxorubicin immunoconjugate. Cancer Immunol Immunother 38:92-98.

Silhavy T J, Berman M L, Enquist L W & Cold Spring Harbor Laboratory. (1984) Experiments with Gene Fusions. Cold Spring Harbor Laboratory, Cold Spring Harbor, N.Y.

Sivam G P, Martin P J, Reisfeld R A & Mueller B M (1995) Therapeutic efficacy of a doxorubicin immunoconjugate in a preclinical model of spontaneous metastatic human melanoma. Cancer Res 55:2352-2356.

Smith G P (1985) Filamentous fusion phage: novel expression vectors that display cloned antigens on the virion surface. Science 228:1315-1317.

Smith T F & Waterman M (1981) Comparison of Biosequences. Adv Appl Math 2:482-489.

Smyth M J, Pietersz G A & McKenzie I F (1987) The cellular uptake and cytotoxicity of chlorambucil-monoclonal antibody conjugates. Immunol Cell Biol 65:315-321.

Staba M J, Wickham T J, Kovesdi I & Hallahan D E (2000) Modifications of the fiber in adenovirus vectors increase tropism for malignant glioma models. Cancer Gene Ther 7:13-19.

Starling J J, Maciak R S, Hinson N A, Nichols C L, Briggs S L, Laguzza B C, Smith W & Corvalan J R (1992) In vivo antitumor activity of a panel of four monoclonal antibody-vinca alkaloid immunoconjugates which bind to three distinct epitopes of carcinoembryonic antigen. Bioconjug Chem 3:315-322.

Stewart J M & Young J D (1969) Solid Phase Peptide Synthesis, Freeman, San Francisco.

Tang X B & Casey J R (1999) Trapping of inhibitor-induced conformational changes in the erythrocyte membrane anion exchanger AE1. Biochemistry 38:14565-14572.

Tavitian B, Terrazzino S, Kuhnast B, Marzabal S, Stettler O, Dolle F, Deverre J R, Jobert A, Hinnen F, Bendriem B, Crouzel C & Di Giamberardino L (1998) In vivo imaging of oligonucleotides with positron emission tomography. Nat Med 4:467-471.

Tijssen (1993) Laboratory Techniques in Biochemistry and Molecular Biology-Hybridization with Nucleic Acid Probes. Elsevier, New York.

Tolsma S S, Volpert O V, Good D J, Frazier W A, Polverini P J & Bouck N (1993) Peptides derived from two separate domains of the matrix protein thrombospondin-1 have anti-angiogenic activity. J Cell Biol 122:497-511.

Tung C H, Zhu T, Lackland H & Stein S (1992) An acridine amino acid derivative for use in Fmoc peptide synthesis. Pept Res 5:115-118.

Urge L, Otvos L, Jr., Lang E, Wroblewski K, Laczko I & Hollosi M (1992) Fmoc-protected, glycosylated asparagines potentially useful as reagents in the solid-phase synthesis of N-glycopeptides. Carbohydr Res 235:83-93

U.S. Pat. No. 4,235,871
U.S. Pat. No. 4,244,946
U.S. Pat. No. 4,551,482
U.S. Pat. No. 4,554,101
U.S. Pat. No. 5,011,634
U.S. Pat. No. 5,088,499
U.S. Pat. No. 5,147,631
U.S. Pat. No. 5,168,037
U.S. Pat. No. 5,223,409
U.S. Pat. No. 5,234,933
U.S. Pat. No. 5,264,563
U.S. Pat. No. 5,326,902
U.S. Pat. No. 5,490,840
U.S. Pat. No. 5,498,538
U.S. Pat. No. 5,508,020
U.S. Pat. No. 5,510,103
U.S. Pat. No. 5,645,815
U.S. Pat. No. 5,578,629
U.S. Pat. No. 5,574,172
U.S. Pat. No. 5,650,489
U.S. Pat. No. 5,651,991
U.S. Pat. No. 5,667,988
U.S. Pat. No. 5,688,931
U.S. Pat. No. 5,702,892
U.S. Pat. No. 5,707,605
U.S. Pat. No. 5,714,166
U.S. Pat. No. 5,738,837
U.S. Pat. No. 5,738,996
U.S. Pat. No. 5,747,334
U.S. Pat. No. 5,756,291
U.S. Pat. No. 5,780,225
U.S. Pat. No. 5,786,387
U.S. Pat. No. 5,811,392
U.S. Pat. No. 5,811,512
U.S. Pat. No. 5,811,515
U.S. Pat. No. 5,817,757
U.S. Pat. No. 5,817,879
U.S. Pat. No. 5,824,483
U.S. Pat. No. 5,830,856

U.S. Pat. No. 5,840,479
U.S. Pat. No. 5,580,717
U.S. Pat. No. 5,851,818
U.S. Pat. No. 5,855,900
U.S. Pat. No. 5,858,410
U.S. Pat. No. 5,858,670
U.S. Pat. No. 5,858,784
U.S. Pat. No. 5,865,754
U.S. Pat. No. 5,922,356
U.S. Pat. No. 5,948,635
U.S. Pat. No. 5,922,545
U.S. Pat. No. 5,928,627
U.S. Pat. No. 5,948,767
U.S. Pat. No. 5,994,392
U.S. Pat. No. 6,013,638
U.S. Pat. No. 6,015,561
U.S. Pat. No. 6,015,881
U.S. Pat. No. 6,022,737
U.S. Pat. No. 6,024,938
U.S. Pat. No. 6,031,071
U.S. Pat. No. 6,083,486
U.S. Pat. No. 6,056,938
U.S. Pat. No. 6,057,098
U.S. Pat. No. 6,068,829
U.S. Pat. No. 6,071,890
U.S. Pat. No. 6,080,384
U.S. Pat. No. 6,106,866
U.S. Pat. No. 6,107,059
U.S. Pat. No. 6,132,766
U.S. Pat. No. 6,136,295
U.S. Pat. No. 6,156,511
U.S. Pat. No. 6,159,443
U.S. Pat. No. 6,168,912
U.S. Pat. No. 6,174,708
U.S. Pat. No. 6,180,348
U.S. Pat. No. 6,197,333
U.S. Pat. No. 6,200,598
U.S. Pat. No. 6,210,707
U.S. Pat. No. 6,214,553
U.S. Pat. No. 6,217,886
U.S. Pat. No. 6,221,018
U.S. Pat. No. 6,225,447
U.S. Pat. No. 6,231,834
U.S. Pat. No. 6,245,318
U.S. Pat. No. 6,246,901
U.S. Pat. No. 6,254,852

Vasavada H A, Ganguly S, Germino F J, Wang Z X & Weissman S M (1991) A contingent replication assay for the detection of protein-protein interactions in animal cells. Proc Natl Acad Sci U S A 88:10686-10690.

Vinogradov S A, Lo L W, Jenkins W T, Evans S M, Koch C & Wilson D F (1996) Noninvasive imaging of the distribution in oxygen in tissue in vivo using near-infrared phosphors. Biophys J 70:1609-1617.

Virgolini I, Traub T, Novotny C, Leimer M, Fuger B, Li S R, Patri P, Pangerl T, Angelberger P, Raderer M, Andreae F, Kurtaran A & Dudczak R (2001) New trends in peptide receptor radioligands. Q J Nucl Med 45:153-159.

Voest E E, Kenyon B M, O'Reilly M S, Truitt G, D'Amato R J & Folkman J (1995) Inhibition of angiogenesis in vivo by interleukin 12. J Natl Cancer Inst 87:581-586.

Walther W & Stein U (1999) Therapeutic genes for cancer gene therapy. Mol Biotechnol 13:21-28.

Weissleder R, Bogdanov A & Papisov M (1992) Drug targeting in magnetic resonance imaging. Magn Reson Q 8:55-63.

Weissleder R, Tung C H, Mahmood U & Bogdanov A, Jr. (1999) In vivo imaging of tumors with protease-activated near-infrared fluorescent probes. Nat Biotechnol 17:375-378.

Wickham T J, Carrion M E & Kovesdi I (1995) Targeting of adenovirus penton base to new receptors through replacement of its RGD motif with other receptor-specific peptide motifs. Gene Ther 2:750-756.

Wilbur D S (1992) Radiohalogenation of proteins: an overview of radionuclides, labeling methods, and reagents for conjugate labeling. Bioconjug Chem 3:433-470

WO 01/09611
WO 93/25521
WO 98/10795
WO 99/54728

Woltering E A, Barrie R, O'Dorisio T M, Arce D, Ure T, Cramer A, Holmes D, Robertson J & Fassler J (1991) Somatostatin analogues inhibit angiogenesis in the chick chorioallantoic membrane. J Surg Res 50:245-251.

Yang M, Wu Z & Fields S (1995) Protein-peptide interactions analyzed with the yeast two-hybrid system. Nucleic Acids Res 23:1152-1156.

Yoo T M, Chang H K, Choi C W, Webber K O, Le N, Kim I S, Eckelman W C, Pastan I, Carrasquillo J A & Paik C H (1997) Technetium-99m labeling and biodistribution of anti-TAC disulfide-stabilized Fv fragment. J Nucl Med 38:294-300.

It will be understood that various details of the invention can be changed without departing from the scope of the invention. Furthermore, the foregoing description is for the purpose of illustration only, and not for the purpose of limitation—the invention being defined by the claims appended hereto.

What is claimed is:

1. A method for identifying a peptide that binds a radiation induced target in an irradiated tumor in a subject, the method comprising:
  (a) exposing a tumor in a subject to ionizing radiation;
  (b) administering to the subject a library of phage-displayed peptides wherein: (i) the phage-displayed peptides are 5-100 amino acids in length; and (ii) the administering step is performed about 4 hours to about 24 hours following he exposing step;
  (c) procuring from the subject the irradiated tumor or a fraction thereof;
  (d) isolating at least one phage from the procured irradiated tumor or from the a fraction thereof, wherein the at least one phage is bound to a radiation induced target in the procured irradiated tumor or the fraction thereof via a peptide displayed on its surface; and
  (e) identifying the peptide displayed on the surface of the phage that binds to the radiation-induced target in the irradiated tumor in the subject.

2. The method of claim 1, wherein the phage-displayed peptides are up to 50 amino acids in length.

3. The method of claim 2, wherein the phage-displayed peptides are 5-11 amino acids in length.

4. The method of claim 3, wherein the phage-displayed peptides are 9-11 amino acids in length.

5. The method of claim 1, wherein the exposing comprises exposing the tumor to less than about 2 Gy ionizing radiation.

6. The method of claim 1, wherein the exposing comprises exposing the tumor to at least about 2 Gy ionizing radiation.

7. The method of claim 6, wherein the exposing comprises exposing the tumor to about 2 Gy to about 6 Gy ionizing radiation.

8. The method of claim 6, wherein the exposing comprises exposing the tumor to about 10 Gy to about 20 Gy ionizing radiation.

9. The method of claim 1, further comprising pre-selecting the library by administering the library to isolated tumor cells or to isolated proteins prior to administering the library to the subject.

10. The method of claim 1, wherein the administering comprises administering the library intravascularly.

11. The method of claim 1, wherein the subject is a warm-blooded vertebrate.

12. The method of claim 11, wherein the subject is a human.

13. The method of claim 1, wherein the library of phage-displayed peptides comprises at least ten peptides.

14. The method of claim 13, wherein the library of phage-displayed peptides comprises at least one hundred peptides.

15. The method of claim 14, wherein the library of phage-displayed peptides comprises at least a billion peptides.

16. The method of claim 1, wherein the diversity of the library is about $10^7$.

17. The method of claim 1, wherein the peptide displayed on the surface of the phage that binds to the radiation induced target in the irradiated tumor binds to a tumor cell, to an endothelial cell associated with tumor vasculature, or to a blood component.

18. The method of claim 1, wherein each of the exposing, administering, and isolating steps is repeated one or more times.

19. The method of claim 1, wherein the phage is a T7 phage.

20. The method of claim 1, wherein the phage is an M13 phage or an M13-derived phage.

21. The method of claim 1, wherein the identifying step further comprises sequencing at least a portion of a genome of the isolated phage to determine an amino acid sequence of the peptide.

22. The method of claim 21, wherein the sequencing is of an amplified fragment comprising a nucleotide sequence encoding the peptide.

* * * * *